(12) United States Patent
Hazama et al.

(10) Patent No.: US 10,980,546 B2
(45) Date of Patent: Apr. 20, 2021

(54) HEMOSTATIC DEVICE

(71) Applicant: TERUMO KABUSHIKI KAISHA, Tokyo (JP)

(72) Inventors: Kenichi Hazama, Bear, DE (US);
Teppei Hayashi, Bear, DE (US);
Ryosuke Maeda, Shizuoka (JP);
Junichi Kobayashi, Shizuoka (JP);
Masako Miyashita, Shizuoka (JP);
Satoshi Wada, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 181 days.

(21) Appl. No.: 16/238,770

(22) Filed: Jan. 3, 2019

(65) Prior Publication Data
US 2019/0150938 A1 May 23, 2019

Related U.S. Application Data

(63) Continuation of application No. PCT/JP2017/024389, filed on Jul. 3, 2017.

(30) Foreign Application Priority Data

Jul. 6, 2016 (JP) .............................. JP2016-134607

(51) Int. Cl.
*A61B 17/135* (2006.01)
*A61B 17/132* (2006.01)
(Continued)

(52) U.S. Cl.
CPC ........ *A61B 17/135* (2013.01); *A61B 17/1325* (2013.01); *A61B 2017/00557* (2013.01);
(Continued)

(58) Field of Classification Search
CPC .............. A61B 17/135; A61B 17/1355; A61B 17/1322; A61B 17/1325; A61B 17/1327; A61B 17/132
See application file for complete search history.

(56) References Cited

U.S. PATENT DOCUMENTS 3,633,567 A 1/1972 Sarnoff
2006/0095072 A1* 5/2006 TenBrink ........... A61B 17/1327
606/201

(Continued)

FOREIGN PATENT DOCUMENTS

CN 201806747 U 4/2011
CN 202027653 U 11/2011
(Continued)

OTHER PUBLICATIONS

International Search Report (PCT/ISA/210) dated Sep. 19, 2017, by the Japanese Patent Office as the International Searching Authority for International Application No. PCT/JP2017/024389.
(Continued)

*Primary Examiner* — Wade Miles
(74) *Attorney, Agent, or Firm* — Buchanan Ingersoll & Rooney PC

(57) ABSTRACT

A hemostatic device including a band that is wrapped around a limb of a living body at a site of the living body where bleeding is to be stopped and an inflatable portion which is inflated by injection of gas to cause the inflatable portion to press the site where bleeding is to be stopped. The hemostatic device includes an injection part that injects gas into the interior of the inflatable portion. The injection part includes a hole penetrating the injection part and communicating the housing space with outside environment. The hemostatic device includes a first support plate and a second support plate positioned adjacent one another along the longitudinal direction of the band. The second support plate
(Continued)

is movably connected to the first support plate. The inflatable portion is on the first support plate and the injection part is on the second support plate.

20 Claims, 13 Drawing Sheets

(51) Int. Cl.
  *A61B 17/12* (2006.01)
  *A61B 90/00* (2016.01)
  *A61B 17/00* (2006.01)
(52) U.S. Cl.
  CPC .............. *A61B 2017/00778* (2013.01); *A61B 2017/00907* (2013.01); *A61B 2017/00955* (2013.01); *A61B 2017/12004* (2013.01); *A61B 2090/0807* (2016.02)

(56) References Cited

U.S. PATENT DOCUMENTS

| | | | | |
|---|---|---|---|---|
| 2011/0028934 | A1* | 2/2011 | Buckman | A61B 17/135 |
| | | | | 604/385.12 |
| 2012/0221041 | A1* | 8/2012 | Hansson | A61B 17/1325 |
| | | | | 606/203 |
| 2013/0237866 | A1* | 9/2013 | Cohen | A61B 5/0036 |
| | | | | 600/502 |
| 2014/0012313 | A1 | 1/2014 | Finkielsztein | |
| 2014/0142615 | A1* | 5/2014 | Corrigan, Jr. | A61B 17/1325 |
| | | | | 606/201 |
| 2015/0119773 | A1 | 4/2015 | Flannery et al. | |
| 2015/0327871 | A1* | 11/2015 | Fortson | A61B 17/135 |
| | | | | 606/202 |
| 2016/0206298 | A1* | 7/2016 | Keene | A61B 17/1325 |
| 2016/0271004 | A1* | 9/2016 | Erdinc | A61B 5/02141 |

FOREIGN PATENT DOCUMENTS

| | | |
|---|---|---|
| CN | 203789981 U | 8/2014 |
| CN | 204839636 U | 12/2015 |
| EP | 2070483 A2 | 6/2009 |
| JP | S5146989 B1 | 12/1976 |
| JP | S6129705 U | 2/1986 |
| JP | 5146989 B2 | 2/2013 |
| JP | 2014521368 A | 8/2014 |
| WO | 2011076640 A1 | 6/2011 |
| WO | 2016095038 A1 | 6/2016 |

OTHER PUBLICATIONS

Written Opinion (PCT/ISA/237) dated Sep. 19, 2017, by the Japanese Patent Office as the International Searching Authority for International Application No. PCT/JP2017/024389.

An English Translation of the International Search Report (Form PCT/ISA/210) and the Written Opinion of the International Searching Authority (Form PCT/ISA/237) dated Sep. 19, 2017, by the Japanese Patent Office in corresponding International Application No. PCT/JP2017/024389. (7 pages).

Chinese Office Action dated Jan. 6, 2021 issued by the Chinese Patent Office in corresponding Chinese Patent Application No. 201780041735.0, with English translation (13 pages).

* cited by examiner

HEMOSTATIC DEVICE

CROSS-REFERENCES TO RELATED APPLICATIONS

This application is a continuation of International Application No. PCT/JP2017/024389 filed on Jul. 3, 2017 and claims priority to Japanese Application No. 2016-134607 filed on Jul. 6, 2016, the entire content of both of which is incorporated herein by reference.

TECHNICAL FIELD

The present invention generally relates to a hemostatic device for performing hemostasis by pressing a punctured site.

BACKGROUND DISCUSSION

Percutaneous treatment/examination, etc. has recently been performed by puncturing a blood vessel of an arm, a leg, etc. of a living body, introducing an introducer sheath into the living body through a puncture site, and delivering a medical instrument such as a catheter to a lesion through a lumen of the introducer sheath. When such treatment/examination, etc. is performed, an operator needs to perform hemostasis in the puncture site after withdrawing the introducer sheath. One known hemostatic device for performing hemostasis includes means for securing a band wrapped around a limb such as an arm or a leg (i.e., securing the band in a state in which the band is wrapped around the limb), and an inflatable portion that is disposed between the band and the limb and is inflated by injection of a fluid to press a puncture site.

When such a hemostatic device is used, in general, a doctor or a nurse connects a dedicated instrument such as a syringe separate from the hemostatic device to a port communicating with an inflatable portion of the hemostatic device and injects a fluid into the inflatable portion using the dedicated instrument, thereby inflating the inflatable portion of the hemostatic device.

Japanese Patent Application Publication No. 2014-521368 discloses a hemostatic device that includes an injection part (pressure pump) capable of injecting gas to an inflatable portion (by being attached to the inflatable portion). Specifically, the injection part is provided with a housing space capable of housing gas and a gas intake hole portion communicating with the housing space. When the injection part is deformed (contracted) in a state in which the hole portion is blocked with a finger, gas housed in the injection part is injected into the inflatable portion. Since the inflatable portion can be inflated by the injection part attached to the inflatable portion, it is possible to eliminate an effort of the doctor or the nurse to carry a separate dedicated instrument or an effort to connect the separate dedicated instrument to the hemostatic device. In addition, it is possible to prevent a situation in which the dedicated instrument is lost and a fluid may not be injected into the inflatable portion.

SUMMARY

In the hemostatic device disclosed in Japanese Patent Application Publication No. 2014-521368, the injection part is provided to protrude from a long axis of a band (i.e., the extending direction of a band) to a side of a limb such as an arm or a leg. For this reason, there is a possibility that the injection part may hinder bending motion of the arm, the leg, etc., and/or the injection part may come in contact with the limb to make a wearer feel uncomfortable.

In addition, the hemostatic device disclosed in Japanese Patent Application Publication No. 2014-521368 has a structure in which the inflatable portion and the injection part are integrally connected via the band. For this reason, when an operation of deforming the injection part is performed at the time of injecting gas into the inflatable portion, an operating force (pressing force) applied to the injection part is easily transmitted to the inflatable portion. As a result, there is a possibility that an inadvertent force may be transmitted to a hemostasis site of a patient where the inflatable portion is disposed.

The hemostatic device disclosed here is capable of inflating an inflatable portion without using a separate dedicated instrument and suppressing transmission of an inadvertent force to a hemostasis site of a patient at the time of performing an operation of inflating the inflatable portion.

A hemostatic device includes a band for wrapping around a site where bleeding is to be stopped of a limb, means for securing that secures the band to the limb in a wrapped state, an inflatable portion that is inflated by injection of gas to press the site where bleeding is to be stopped, an injection part having a housing space capable of housing gas and being capable of injecting gas housed in the housing space into the inflatable portion, and a support plate connected to the band. The support plate includes a first support plate disposed on a long axis of the band. The inflatable portion is disposed on the first support plate, and a second support plate is disposed on the long axis of the band and movably connected to the first support plate. The injection part includes a hole portion penetrating the injection part and communicating with the housing space, and is disposed on the second support plate.

In another aspect, the disclosure involves a hemostatic device including a band configured to be wrapped around a limb of a living body at a site of the living body where bleeding is to be stopped, a first support plate connected to the first end of the band and a second support plate connected to the second end of the band. The first support plate possesses an inner surface facing toward the limb when the band is wrapped around the limb and an outer surface facing away from the limb when the band is wrapped around the limb and the second support plate possesses an inner surface facing toward the limb when the band is wrapped around the limb and an outer surface facing away from the limb when the band is wrapped around the limb. The first and second support plates are more rigid than the band. The device includes an inflator on the inner surface of the first support plate so that when the band is wrapped around the limb of the living body the inflator is positioned between the first support plate and the limb of the living body. The inflator is inflated by injection of gas into the interior to expand the exterior and cause the inflator to press the site where bleeding is to be stopped. The hemostatic device includes an injector on the outer surface of the second support plate so that when the band is wrapped around the limb of the living body the second support plate is positioned between the injector and the limb of the living body. The injector includes a bottom part, a vertical wall and a top part collectively defining an interior space configured to house a gas. The injection part includes a hole, the outside environment communicating with the interior space of the injection part via the hole. The hemostatic device includes a tube connecting the interior of the inflator to the interior space of the injector, and the injector is configured to inject the gas housed in the housing space into the interior of the inflatable portion through the tube when the hole is covered and the vertical wall of the injector is simultaneously pressed.

In yet another aspect, the disclosure involves a method including wrapping a band of a hemostatic device around a limb of a living body at a site on the living body at which bleeding is to be stopped, the hemostatic device including an inflatable portion and an injection portion, the inflatable portion including an outer wall defining an interior space, the inflatable portion being deflated when the band is wrapped around the limb of the living body, the injection portion including an outwardly protruding vertical wall and a hole. The method includes pressing the outwardly protruding vertical wall of the injection portion while simultaneously covering the hole to deform the injection portion towards the limb of the living body, the pressing of the outwardly protruding vertical wall of the injection portion causing gas to enter the interior space of the inflatable portion, inflate the inflatable portion and apply pressure to the site on the limb of the living body to stop bleeding at the bleeding site of the limb. The method also includes gradually reducing the pressure applied to the limb According to the hemostatic device configured as described above, gas is injected into the inflatable portion by the injection part communicating with the inflatable portion. For this reason, a doctor or a nurse can inflate the inflatable portion without using a separate dedicated instrument. In addition, the injection part is disposed on the second support plate and rarely comes into contact with the limb, and thus it is possible to reduce discomfort felt by the wearer. The injection part is disposed on the second support plate at a different position relative to that of the first support plate on which the inflatable portion is disposed, and the second support plate is movably disposed with respect to the first support plate. It is thus possible to help suppress transmission of an inadvertent force from the injection part to the hemostasis site at the time of sending gas from the injection part to the inflatable portion. Therefore, the hemostatic device may reduce the labor of an operator (i.e., difficulty of operation) and suppress transmission of an inadvertent force to a hemostasis site of a patient by integrally providing the hemostatic device and the injection part for injecting gas into the hemostatic device.

BRIEF DESCRIPTION OF THE DRAWINGS

FIG. 6A is a diagram illustrating a state in which air is injected into an inflatable portion, and FIG. 6B is a diagram illustrating a state in which inflation of the inflatable portion is completed.

DETAILED DESCRIPTION

Figure 1:
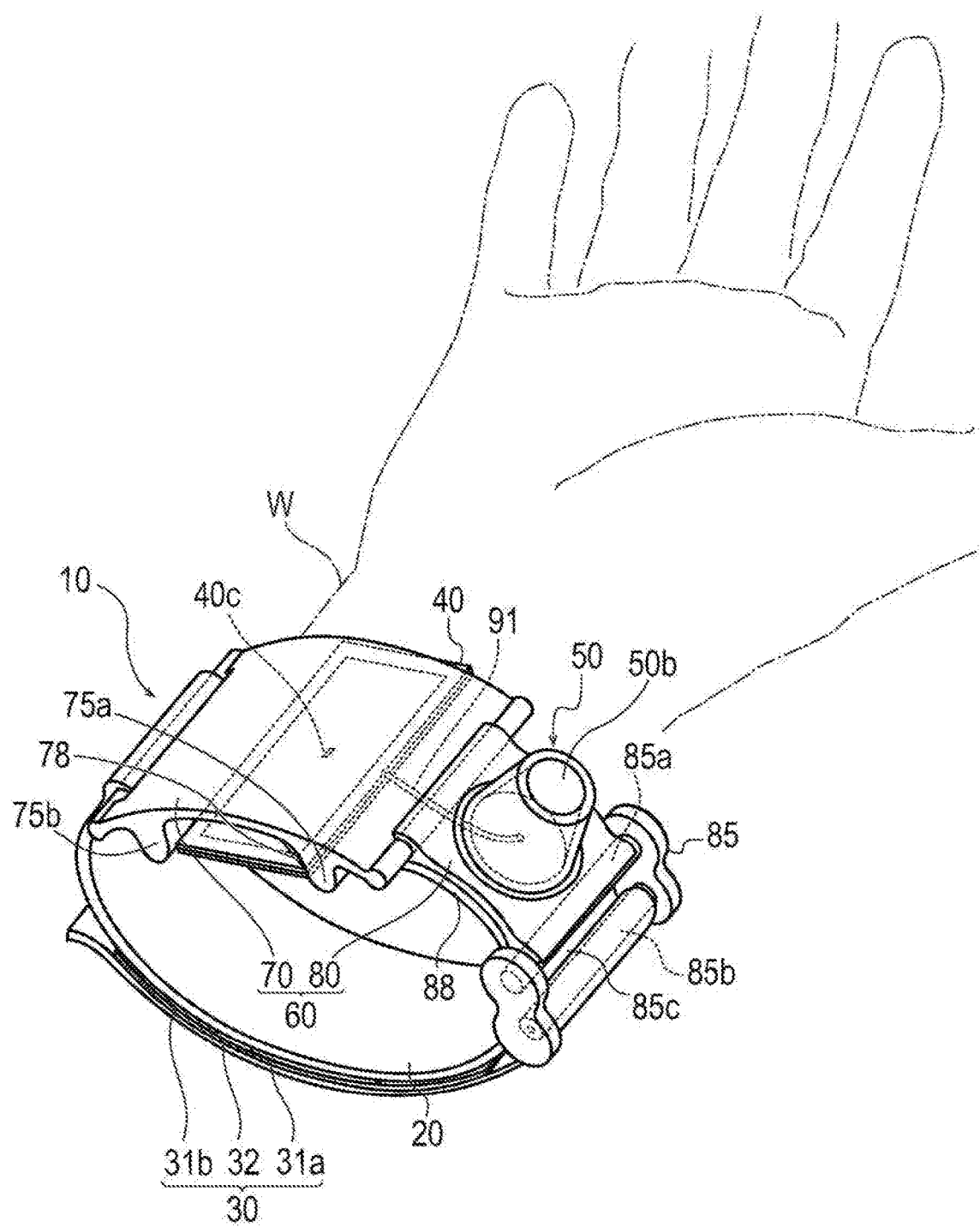
FIG. 1 is a schematic perspective view of a hemostatic device according to an embodiment.

Set forth below with reference to the accompanying drawings is a detailed description of embodiments of a hemostatic device representing examples of the inventive hemostatic device disclosed here. Note that the description below does not restrict the technical scope or the meaning of a term described in claims. In addition, a ratio of dimensions in the drawings is exaggerated for convenience and may be different from an actual ratio.

A hemostatic device 10 according to the present embodiment will be described with reference to FIG. 1 to FIG. 10. FIG. 1 to FIG. 6B are diagrams that illustrate examples of each portion of the hemostatic device 10. FIG. 7 to FIG. 10 are diagrams that illustrate an exemplary use of the hemostatic device 10.

Figure 7:
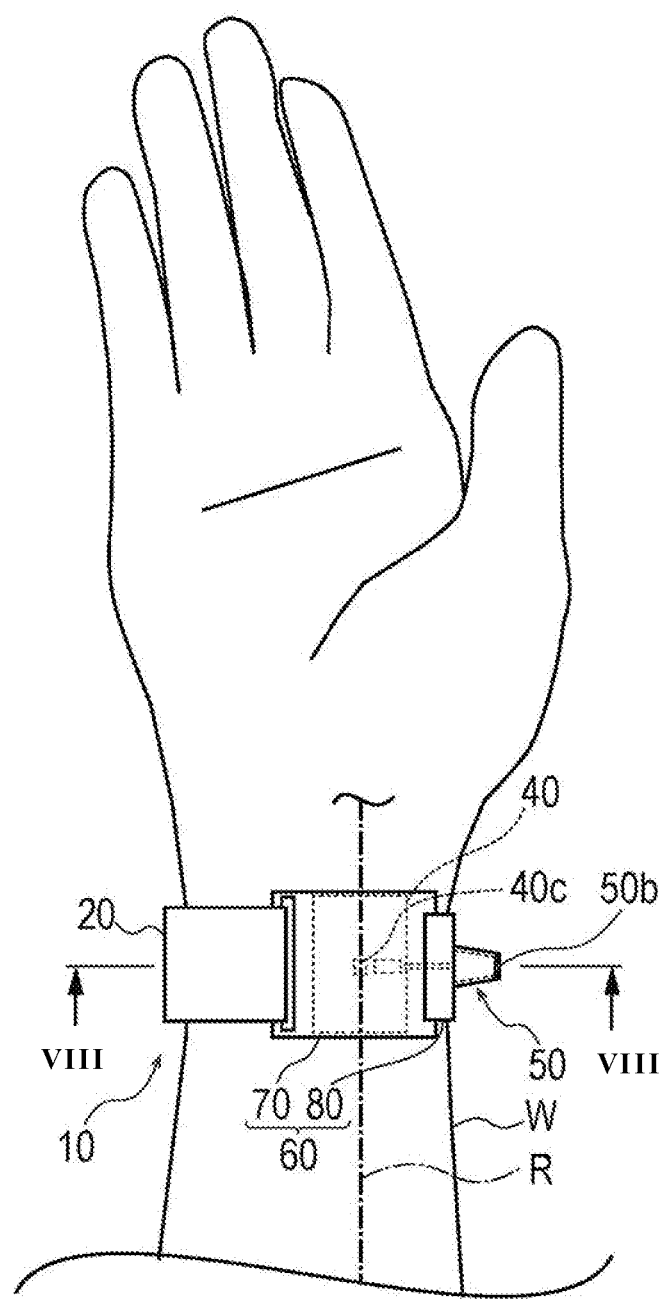
FIG. 7 is a plan view illustrating a state in which the hemostatic device according to the embodiment shown in FIG. 1 is mounted on a wrist.
Figure 9:
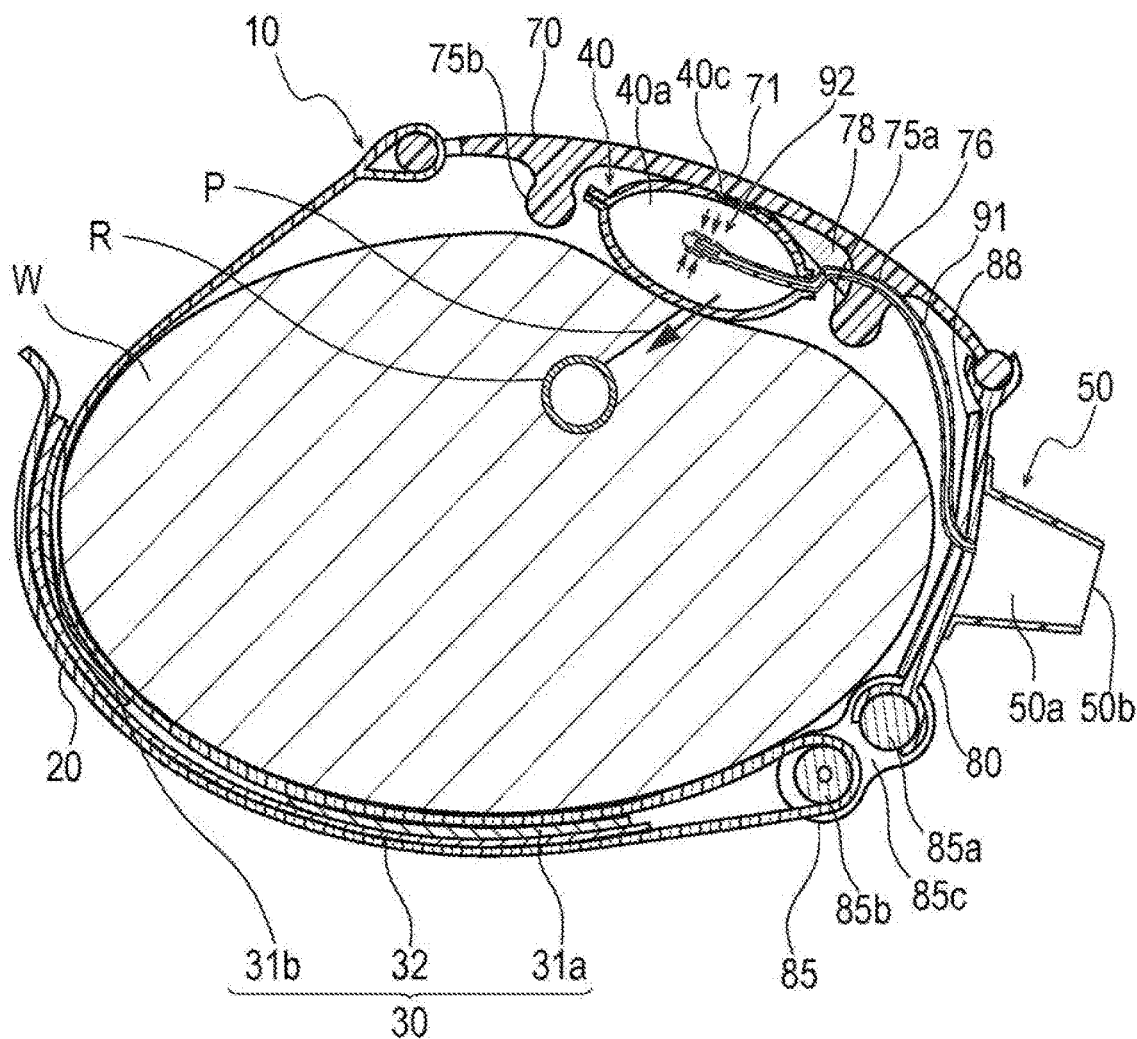
FIG. 9 is a cross-sectional view taken along VIII-VIII line of FIG. 7, and is a diagram illustrating a state in which inflation of the inflatable portion is completed.

As illustrated in FIG. 7 and FIG. 9, after withdrawing an introducer sheath indwelled in a puncture site P (corresponding to a "site where bleeding is to be stopped") formed in a radial artery R of a wrist W (corresponding to a "limb"), the hemostatic device 10 according to the embodiment is used to stop bleeding in the puncture site P. For example, the introducer sheath may be used to insert a catheter, etc. for performing treatment/examination, etc. into a blood vessel of the living body.

As illustrated in FIG. 1 and FIG. 9, the hemostatic device 10 includes a band 20 for wrapping around the wrist W (i.e., configured to be wrapped around a limb of a living body), a surface fastener 30 (corresponding to "means for securing" or a "securing member") that secures the band 20 in a state of being wrapped around the wrist W, and an inflatable portion 40 that inflates when gas (e.g., air) is injected into the inflatable portion 40 and presses the puncture site P. The inflatable portion 40 includes a marker 40c for positioning the inflatable portion 40 at the puncture site P. The hemostatic device 10 also includes an injection part 50 (an injector) capable of injecting air into the inflatable portion 40, a support plate 60 connected to the band 20, and a tube (corresponding to a "flow route") 91 that communicates between the inflatable portion 40 and the injection part 50

(i.e., the inflatable portion 40 is connected to and communicates with the injection part 50 via the tube 91 as shown in FIG. 1).

Figure 3:
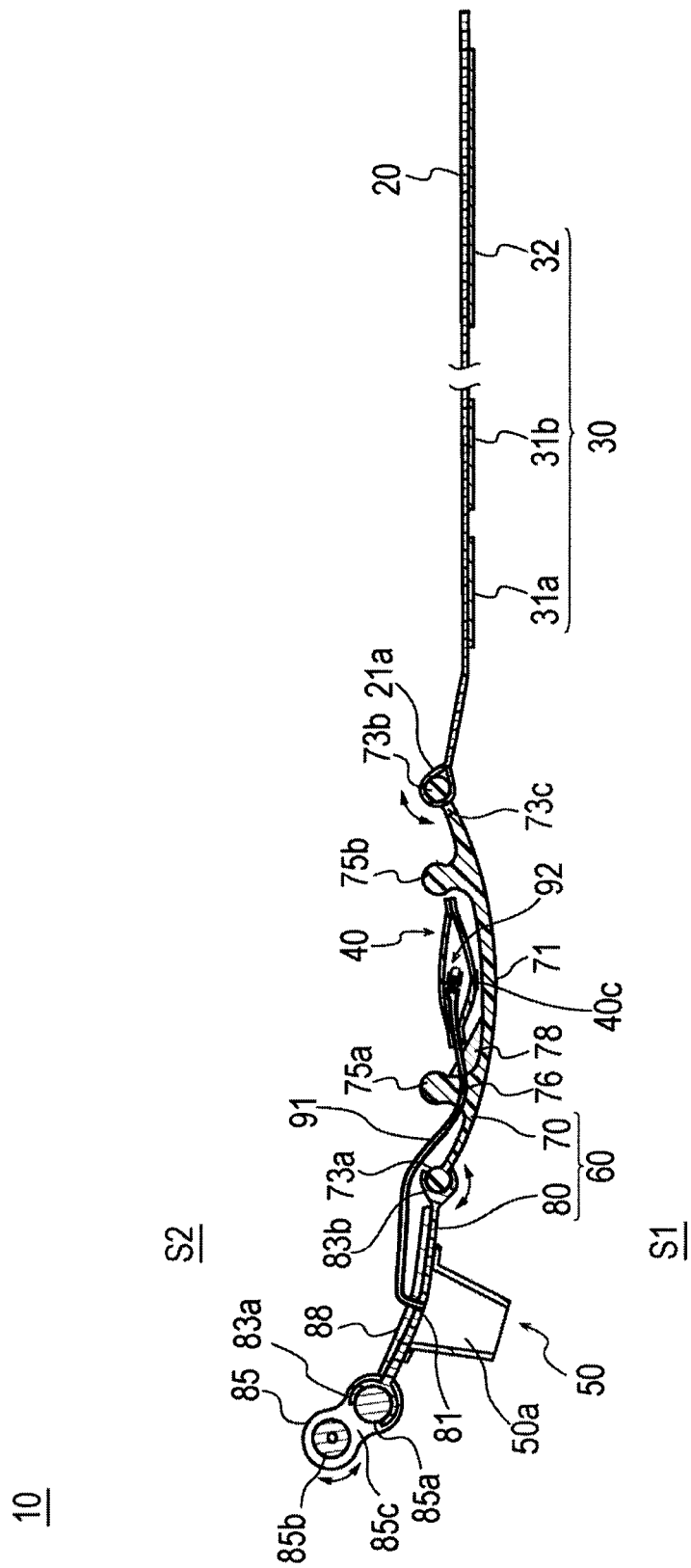
FIG. 3 is a cross-sectional view taken along III-III line of FIG. 2.

Note that in the present specification, when the band 20 is wrapped around a wrist W, a surface of the support plate 60 on a side where the injection part 50 is disposed is referred to as an "outer surface" (corresponding to a "first surface"), and a surface (mounting surface) of the support plate 60 on a side facing a body surface of the wrist W where the inflatable portion 40 is disposed is referred to as an "inner surface" (corresponding to a "second surface"). In FIG. 3, an outer surface side is labeled S1, and an inner surface side is labeled S2.

Figure 2:
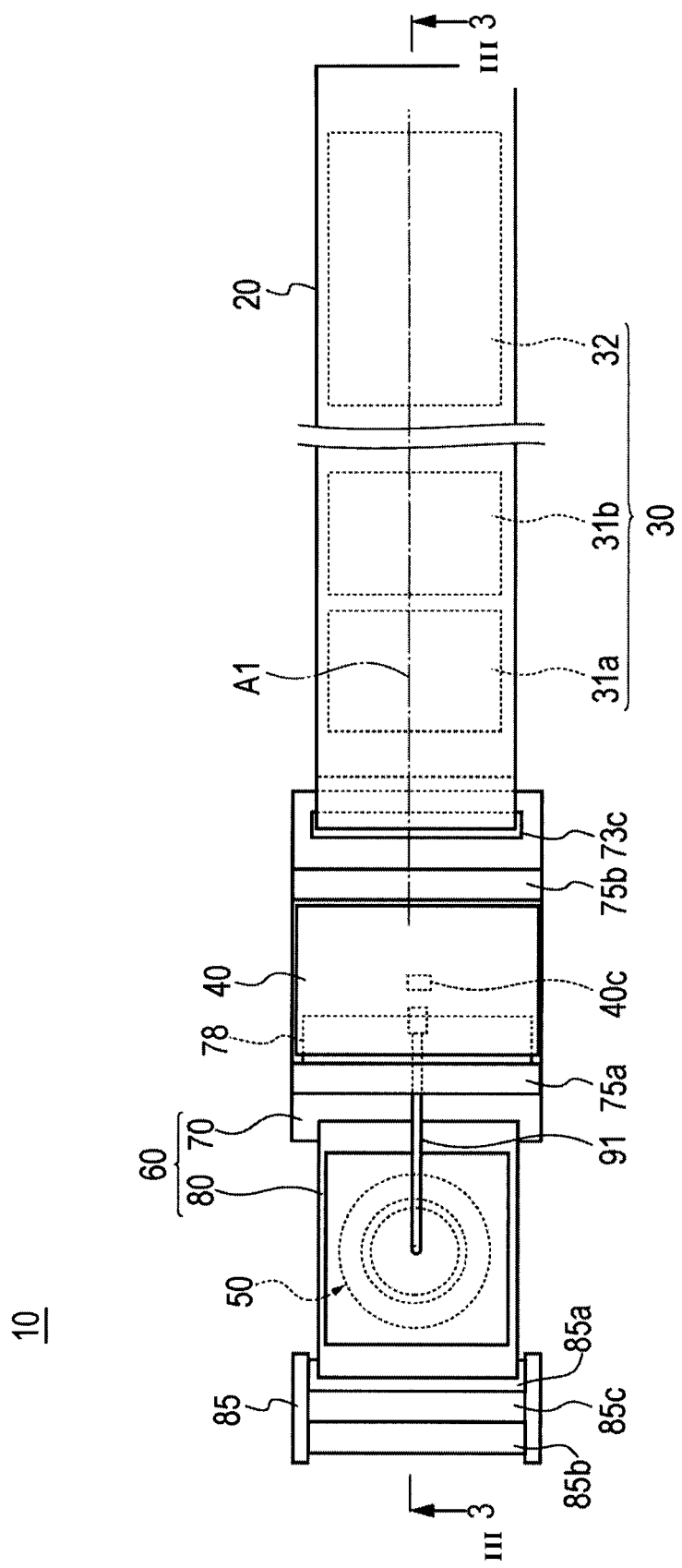
FIG. 2 is a plan view of the hemostatic device according to the embodiment shown in FIG. 1 viewed from an inner surface side.

As illustrated in FIG. 1 to FIG. 3, the support plate 60 (support structure) has a first support plate 70 and a second support plate 80. The inflatable portion 40 is disposed on the first support plate 70 and the injection part 50 is disposed on the second support plate 80.

As illustrated in FIG. 2, the first support plate 70 and the second support plate 80 are disposed on a long axis A1 of the band 20. The long axis A1 of the band 20 indicates an extending direction (longitudinal direction) of the band 20 when the hemostatic device 10 is not mounted on the wrist W (i.e., when the band 20 is extended linearly instead of being wound around a wrist W). That is, the first support plate 70 and the second support plate 80 are disposed at different positions in the extending direction of the band 20, respectively. The inflatable portion 40 disposed on the first support plate 70 and the injection part 50 disposed on the second support plate 80 are thus disposed at different positions on the long axis A1 of the band 20, respectively, similarly to the respective support plates 70 and 80.

The first support plate 70 has a cross-sectional shape curved to protrude to an outer surface side from both end portion sides in a direction of the long axis A1 toward a central portion 71 side as illustrated in FIG. 3. A first connecting portion 73a connected to the second support plate 80 is provided at an end portion of the first support plate 70 on the second support plate 80 side. A second connecting portion 73b connected to the band 20 is provided at an end portion of the first support plate 70 on the band 20 side. The central portion 71 of the first support plate 70 thus protrudes outwardly (i.e., away from the wrist W when the hemostatic device 10 is attached to a patient) from both of these end connecting portions 73a, 73b as shown in FIG. 3.

The second support plate 80 also has a cross-sectional shape curved to protrude to an outer surface side from the both end portion sides in the direction of the long axis A1 toward a central portion 81 side. A first connecting portion 83b connected to the first support plate 70 is provided at an end portion of the second support plate 80 on the first support plate 70 side. A connecting member 85 is disposed at an end portion of the second support plate 80 on an opposite side from where the first connecting portion 83b is provided. The second support plate 80 is connected to the connecting member 85 through the second connecting portion 83a provided at the end portion on the connecting member 85 side.

The shape of each of the support plates 70 and 80, the length (a length dimension) of each of the support plates 70 and 80 along the long axis A of the band 20, etc. are not particularly limited as long as astriction (pressure hemostasis or pressurizing and stopping bleeding) by the hemostatic device 10 can be performed.

Figure 8:
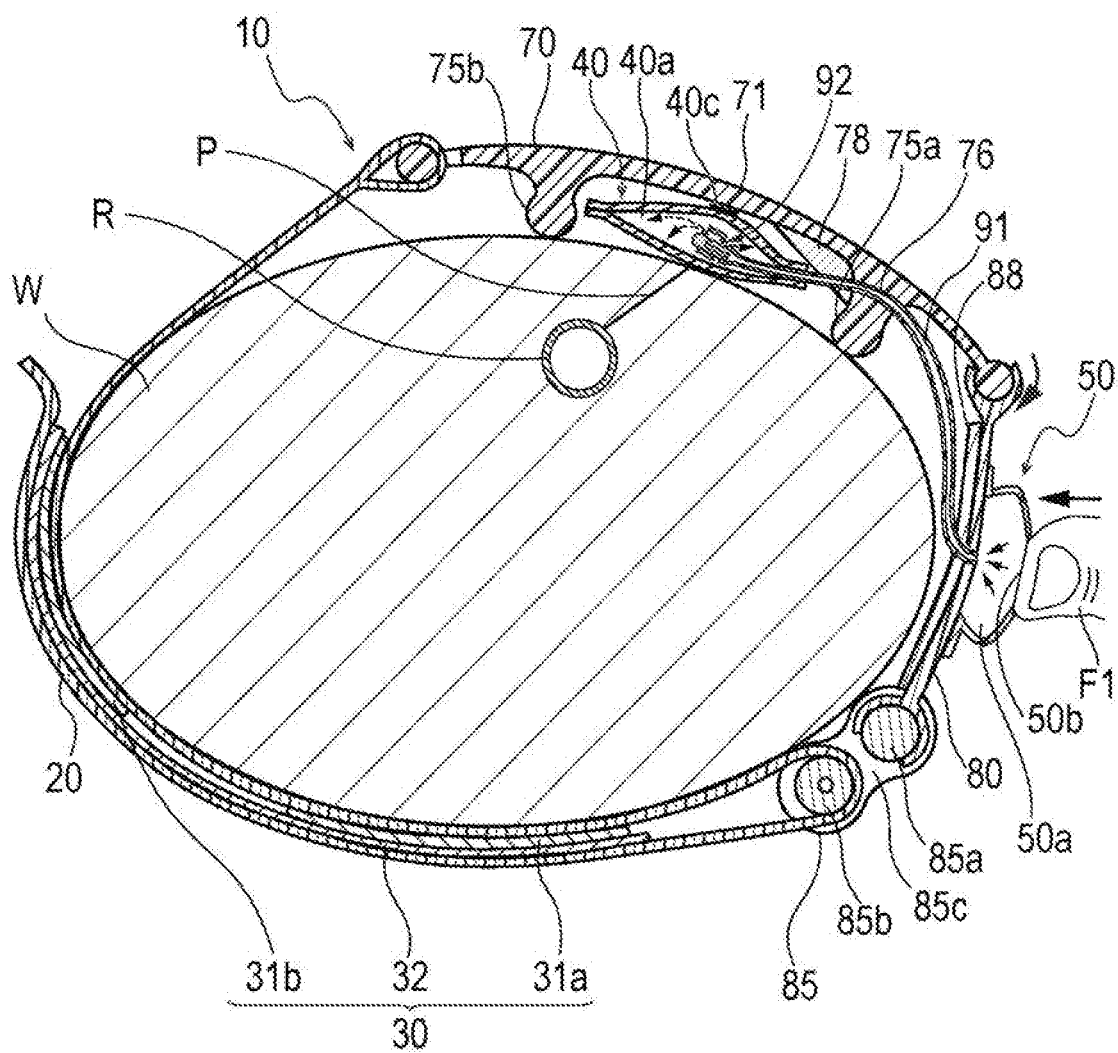
FIG. 8 is a cross-sectional view taken along VIII-VIII line of FIG. 7, and is a diagram illustrating a state in which the inflatable portion is inflated.

The connecting member 85 connects the band 20 and the second support plate 80 when the hemostatic device 10 is mounted on the wrist W. In addition, the connecting member 85 adjusts a length of the band 20 according to a circumferential length of the wrist W (thickness of the wrist) of the wearer. As illustrated in FIG. 3 and FIG. 8, the connecting member 85 has a connecting portion 85a connected to the second support plate 80, a holding portion 85b that holds a part of the band 20 in a folded state, and an insertion portion 85c into which the band 20 can be inserted.

The band 20 is wrapped along a part of an outer periphery of the wrist W. As illustrated in FIGS. 7 and 8, for example, a length of the band 20 can be adjusted such that a range of half or more of the outer periphery of the wrist W is covered when the hemostatic device 10 is mounted on the wrist W (when the palm faces upward).

A connecting end portion 21a connected to the first support plate 70 is provided at an end portion of the band 20 on the first support plate 70 side as shown in FIG. 3.

A surface fastener 30 is disposed on the band 20 as shown in FIGS. 2 and 3. For example, the surface fastener 30 is a hook and loop fastener known as a general product such as VELCRO (registered trademark) or Magic tape (registered trademark). The surface fastener 30 includes two female sides 31a and 31b and one male side 32. As illustrated in FIG. 2 and FIG. 3, the respective female sides 31a and 31b and the male side 32 are disposed on the outer surface side in a state before the hemostatic device 10 is mounted on the wrist W.

The hemostatic device 10 is mounted on the wrist W by wrapping the band 20 around the wrist W while being folded back at the holding portion 85b of the connecting member 85 as shown in FIG. 8. More specifically, the band 20 is folded back at the holding portion 85b of the connecting member 85, thereby causing the male side 32 to face the respective female sides 31a and 31b. When a length in which the band 20 is folded back is adjusted according to an outer periphery length of the wrist W of the wearer, it is possible to appropriately mount the hemostatic device 10 without depending on the wearer (i.e., the band 20 may be easily adjusted for different sized wrists of different patients). The hemostatic device 10 is mounted on the wrist W by joining each of the female sides 31a and 31b and the male side 32 together. In general, the female sides 31a and 31b are more flexible than the male side 32. For this reason, it is possible to help suppress discomfort given to the wearer by disposing the female sides 31a and 31b at positions closer to the outer surface of the wrist W than the male side 32 when the hemostatic device 10 is mounted on the wrist W as illustrated in FIG. 1.

The surface fastener 30 may include, for example, one female side and one male side or may be configured by switching the position of the female side with the position of the made side. In addition, means for securing the band 20 to the wrist W in a wrapped state is not limited to the surface fastener 30. For example, it is possible to use a securing member such as a snap, a button, a clip, or a frame member passing the end portion of the band 20 as the means for securing the band to the wrist W.

The band 20 material is not particularly limited as long as the band 20 has flexibility (i.e., is relatively flexible). Examples of a material for the band 20 include polyvinyl chloride, polyolefins such as polyethylene, polypropylene, polybutadiene and ethylene-vinyl acetate copolymers (EVA), polyesters such as polyethylene terephthalate (PET) and polybutylene terephthalate (PBT), polyvinylidene chloride, silicone, polyurethane, various thermoplastic elastomers such as polyamide elastomers, polyurethane elastomers and polyester elastomers, and an arbitrary combination of the above (blend resin, polymer alloy, laminate, etc.).

The band 20 may be transparent, translucent, or colored transparent, or may be given a specific color.

The first support plate 70 is connected to the second support plate 80 in a relatively movable manner via the first connecting portion 73a of the first support plate 70 and the first connecting portion 83b of the second support plate 80 as illustrated in FIG. 3.

The first connecting portion 73a of the first support plate 70 is formed of a shaft-shaped member (a shaft) having a substantially circular cross-sectional shape. The first connecting portion 83b of the second support plate 80 is a concave groove that is configured to attach to the first connecting portion 73a of the first support plate 70 (i.e., the first connecting portion 73a may fit within the first connecting portion 83b as shown in FIG. 3). The first connecting portion 83b of the second support plate 80 is rotatable along an outer peripheral surface of the first connecting portion 73a in a state of being fit on the first connecting portion 73a of the first support plate 70.

As illustrated in FIG. 3, the first support plate 70 is connected to the band 20 in a relatively movable manner via the second connecting portion 73b of the first support plate 70 and the connecting end portion 21a of the band 20.

The second connecting portion 73b of the first support plate 70 is formed of a shaft-shaped member (a shaft) having a substantially circular cross-sectional shape. The connecting end portion 21a of the band 20 is an end portion of the band 20. The connecting end portion 21a of the band 20 is disposed to wrap around an outer peripheral surface of the second connecting portion 73b of the first support plate 70 as shown in FIG. 3. A gap 73c enabling the connecting end portion 21a of the band 20 to rotate along the outer peripheral surface of the second connecting portion 73b is provided in a vicinity of the second connecting portion 73b of the first support plate 70.

The second support plate 80 and the connecting member 85 are connected to each other via the second connecting portion 83a of the second support plate 80 and the connecting portion 85a of the connecting member 85 as shown in FIG. 3.

The connecting portion 85a of the connecting member 85 is formed of a shaft-shaped member (a shaft) having a substantially circular cross-sectional shape. The second connecting portion 83a of the second support plate 80 is a concave groove that can be fit on the connecting portion 85a of the connecting member 85 (i.e., the connecting portion 85a may fit within the second connecting portion 85a of the second support plate 80 as shown in FIG. 3). The second connecting portion 83a of the second support plate 80 is rotatable along an outer peripheral surface of the connecting portion 85a in a state of being fit on the connecting portion 85a of the connecting member 85.

The holding portion 85b of the connecting member 85 is configured to rotate on the connecting member 85 (i.e., the holding portion 85b is rotatable relative to the remainder of the connecting member 85). When the band 20 is inserted into the insertion portion 85c of the connecting member 85 at the time of mounting the hemostatic device 10 on the wrist W, the holding portion 85b rotates in accordance with insertion of the band 20. The holding portion 85b thus allows an operation of wrapping the band 20 with respect to the wrist W to be smoothly performed by winding/wrapping the band 20 (i.e., advancing the band in a direction of winding the band 20 or a direction of being wrapped on the wrist W).

Each of the first support plate 70 and the second support plate 80 is made of a material more rigid than that of the band 20. The first and second support plates 80 are also configured to maintain a substantially constant curved cross-section shape, which is illustrated in FIG. 3.

As illustrated in FIG. 8, the first support plate 70 has a first protrusion 75a and a second protrusion 75b provided on the inner surface side of the first support plate 70.

The first protrusion 75a is disposed on the second support plate 80 side (i.e., closer to the second support plate 80) of the first support plate 70. The second protrusion 75b is disposed on the band 20 side (i.e., closer to the band 20) of the first support plate 70, and is positioned to interpose the inflatable portion 40 between the first protrusion 75a and the second protrusion 75b along the direction of the long axis A1 of the band 20 (left-right direction of FIG. 8).

The first protrusion 75a and the second protrusion 75b have a function of adjusting a distance between the puncture site P and the first support plate 70 when the hemostatic device 10 is mounted on the wrist W of a patient and the inflatable portion 40 is to be inflated (e.g., the state illustrated in FIG. 8).

When the first support plate 70 is disposed on the wrist W at the time of wrapping the band 20 around the wrist W, the first protrusion 75a and the second protrusion 75b are in contact with the wrist W. When the band 20 is folded back at the connecting member 85 and wrapped around the wrist W in a state in which the first protrusion 75a and the second protrusion 75b are in contact with the wrist W, the distance between the puncture site P and the first support plate 70 is adjusted to a predetermined size according to a height dimension (i.e., the dimension in the protruding direction) of each of the first protrusion 75a and the second protrusion 75b. Similarly, a distance between the inflatable portion 40 disposed on the first support plate 70 and the puncture site P is adjusted to a predetermined size. This configuration allows, for example, the distance between the inflatable portion 40 and the puncture site P before inflation is started to be kept at a predetermined distance irrespective of a difference in outer peripheral length of the wrist W for each wearer. Further, it is possible to apply a certain pressing force regardless of the wearer when inflation is performed in a state in which the distance between the inflatable portion 40 and the puncture site P before start of inflation is adjusted to the predetermined distance.

Each of the first protrusion 75a and the second protrusion 75b may be formed, for example, in a cross-sectional shape in which a distal portion in the protruding direction is rounded. When each of the first protrusion 75a and the second protrusion 75b has such a rounded distal end, an excessive pressing force is prevented from being applied to the wearer at the time of contact with the wrist W.

The height dimension (dimension in the protruding direction) of each of the first protrusion 75a and the second protrusion 75b is not particularly limited as long as the distance between the inflatable portion 40 and the puncture site P before starting inflation can be kept at a predetermined size. For example, the distance may be appropriately set according to a thickness dimension, etc. of the inflatable portion 40 at the time of inflation. In addition, the cross-sectional shape of each of the first protrusion 75a and the second protrusion 75b and a position of the first and second protrusions 75a, 75b on the first support plate 70 are not particularly limited, and may be appropriately changed. Each of the protrusions 75a and 75b may be formed integrally with the first support plate 70 or the protrusions 75a and 75b may be formed as a separate member from the first support plate 70. Each of the protrusions 75a and 75b may also be provided with a cushioning member that alleviates a pressing force at the time of contact with the skin of a patient.

Examples of a constituent material of each of the support plate 70 and 80 include acrylic resins, polyvinyl chloride (particularly rigid polyvinyl chloride), polyolefins such as polyethylene, polypropylene and polybutadiene, polystyrene, poly(4-methyl pentene-1), polycarbonates, ABS resins, polymethyl methacrylate (PMMA), polyacetals, polyarylates, polyacrylonitriles, polyvinylidene fluorides, ionomers, acrylonitrile-butadiene-styrene copolymers, polyesters such as polyethylene terephthalate (PET) and polybutylene terephthalate (PBT), butadiene-styrene copolymers, aromatic or aliphatic polyamides, and fluorocarbon resins such as polytetrafluoroethylene.

It is preferable that at least the part of the first support plate 70 that overlaps with the inflatable portion 40 is substantially transparent. However, the overlapping part may not be transparent, and may be translucent or colored transparent. When at least the part of the first support plate 70 that overlaps the inflatable portion 40 is substantially transparent or translucent, the puncture site P may be reliably visually recognized from the outer surface side, and the marker 40c (described in more detail below) may be easily positioned at the puncture site P.

The inflatable portion 40 has the function of inflating upon injection of air to apply a pressing force to the puncture site P. In the present embodiment, as illustrated in FIG. 1 and FIG. 3, the inflatable portion 40 is formed of a bag-shaped member obtained by superimposing two substantially rectangular sheets and joining circumferences. In this way, an inflatable space 40a is formed between the two sheets. The configuration of the inflatable portion 40 is not particularly limited as long as the inflatable portion 40 can be inflated by injection of air into the interior of the inflatable portion 40. For example, the inflatable portion 40 may be a bag-shaped member formed by folding one sheet and joining edge portions, or a balloon-shaped member that does not have an edge portion. The external shape of the inflatable portion 40 is not particularly limited. For example, the inflatable portion 40 may have an external shape such as a circle, an ellipse, or a polygon in plan view in a state of not being inflated (i.e., when the inflatable portion 40 is deflated).

The inflatable portion 40 is made of a thermosetting elastomer having relatively high gas permeability. For this reason, after the inflatable portion 140 is inflated, air injected into the inflatable portion 140 escapes from the inflatable portion 140 over time to an extent that vascular occlusion can be prevented. The air escapes through the thermosetting elastomer corresponding to a constituent material of the inflatable portion 140 (a state in which air escapes is indicated by a dotted arrow in FIG. 10). As the thermosetting elastomer, for example, it is possible to use silicone, natural rubber, etc. Silicone is preferably used as the thermosetting elastomer from a viewpoint of visibility.

When the inflatable portion 40 is made of the thermosetting elastomer, for example, an adhesive may be used to join the edges of the inflatable portion 40 to form a bag shape. One part of the inflatable portion 40 may be, for example, made of a thermosetting elastomer and another part may be made of a thermoplastic material. When one part is made of thermosetting elastomer and the other part is made of thermoplastic material, the inflatable portion 40 may be formed, for example, using a sheet in which the thermoplastic material and the thermosetting elastomer are integrally molded, a sheet in which a rectangular member made of the thermosetting elastomer is attached to a center of a frame-shaped member made of the thermoplastic material, etc. As the thermoplastic material, for example, it is possible to use a thermoplastic resin such as polyvinyl chloride, polyethylene, polypropylene, or polyvinylidene chloride or various thermoplastic elastomers such as an olefinic thermoplastic elastomer, a styrene thermoplastic elastomer, and a polyethylene thermoplastic elastomer.

As illustrated in FIG. 3, the inflatable portion 40 is disposed at a position overlapping the central portion 71 of the first support plate 70. For this reason, when the inflatable portion 40 is inflated, inflation of the inflatable portion 40 in a direction away from the body surface of the wrist W is suppressed by the first support plate 70 as illustrated in FIG. 9, and thus a pressing force of the inflatable portion 40 is concentrated on (i.e., directed towards) the wrist W side.

The inflatable portion 40 is held on the inner surface side of the first support plate 70 between the first protrusion 75a of the first support plate 70 and the second protrusion 75b of the first support plate 70 as depicted in FIG. 3. The inflatable portion 40 is connected (linked) to the second support plate 80 by a tube 91 which sends air to the interior of the inflatable portion 40. The inflatable portion 40 is connected to the tube 91, so that the inflatable portion 41 is prevented from falling off the hemostatic device 10. Additionally or alternatively, the inflatable portion 40 may be directly connected to the first support plate 70 by being attached and secured to the first support plate 70 or by being detachably held on the first support plate 70 using a mechanical method such as fitting or pinching. A method of connecting the inflatable portion 41 to the first support plate 70 is not particularly limited. As described above, a connection between the band 20 and the inflatable portion 40 is not particularly limited. For example, the band 20 and the inflatable portion 40 may be directly secured (connected), or the inflatable portion 40 may be connected to the band 20 via the tube 91 communicating with the injection part 50 secured to the band 20.

It is preferable that the inflatable portion 40 is substantially transparent. However, the inflatable portion 40 may not be transparent, and may be translucent or colored transparent. In this way, the puncture site P may be visually recognized from the outer surface side, and the marker 40c described below may be easily positioned in the puncture site P by an operator.

As illustrated in FIG. 9, the first support plate 70 has an auxiliary pressing portion 78 disposed on the second protrusion 75b side of the first protrusion 75a (left side in FIG. 9).

The auxiliary pressing portion 78 comes into contact with the inflatable portion 40 when the inflatable portion 40 in an inflated state, and adjusts the pressing direction of the inflatable portion 40 as indicated by an arrow in FIG. 9. Specifically, the pressing direction of the inflatable portion 40 is adjusted to be directed toward the puncture site P by the auxiliary pressing portion 78 when the inflatable portion 40 is inflated.

The cross-sectional shape, size, etc. of the auxiliary pressing portion 78 are not particularly limited as long as an inflating direction of the inflatable portion 40 can be adjusted to a desired direction on the inner surface side of the first support plate 70. The manufacturing cost associated with addition of the auxiliary pressing portion 78 may be reduced by forming the auxiliary pressing portion 78 using a simple member provided on the inner surface side of the first support plate 70 (i.e., on the inner surface of the first support plate 70).

The auxiliary pressing portion 78 may be, for example, made of a sponge-like substance, an elastic material, an aggregate of fibers such as cotton, a combination thereof, etc.

As illustrated in FIG. 3 and FIG. 9, a cushioning member 88 that alleviates a contact force (pressing force) transmitted from the inner surface of the second support plate 80 to the wrist W is disposed on the inner surface (i.e., the opposite surface from where the injection part 50 is disposed) of the second support plate 80. Even when the second support plate 80 and the wrist W are disposed to be in contact with each other while pressure hemostasis is performed when the hemostatic device 10 is mounted on the wrist W, the cushioning member 88 prevents the second support plate 80 from being pressed against the wrist W (to help prevent discomfort to the wearer).

The position at which the cushioning member 88 is provided on the second surface (inner surface) of the second support plate 80, a cross-sectional shape, a thickness, etc. of the cushioning member 88 are not particularly limited as long as transmission of a pressing force from the second surface (inner surface) of the second support plate 80 to the wrist W can be alleviated. For example, when the cross-sectional shape of the second support plate 80 is shaped not to contact the wrist W, and a portion not in contact with the wrist W is provided in a part of the second support plate 80, a position at which the cushioning member 88 is provided may be appropriately changed in accordance with a shape of the second support plate 80 (i.e., the cushioning member 88 may be provided only where the inner surface of the second support plate 80 may contact the patient's skin).

The cushioning member 88 may be, for example, made of a soft resin material, a sponge-like substance, or an elastic material.

The marker 40c is provided at an approximate center of the inflatable portion 40 on a side facing the band 20 as illustrated in FIGS. 2 and 3. When the marker 40c is provided on the inflatable portion 40, the inflatable portion 40 can be easily positioned with respect to (relative to) the puncture site P, and thus position shift of the inflatable portion 40 is suppressed. The marker 40c may be provided on a side of the inflatable portion 40 facing the wrist W (i.e., the inner side). In this instance, it is preferable that the marker 40c is provided on the inner surface of the inflatable portion 40 so as not to directly come into contact with the puncture site P. Note that a position at which the marker 40c is provided is not particularly limited as long as the inflatable portion 40 can be positioned at the puncture site P. For example, the marker 40c may be provided on the first support plate 70 as long as the inflatable portion 40 can be positioned at the puncture site P (by allowing an operator to use the marker 40c as a visual guide to facilitate proper positioning of the inflatable portion 40).

The shape of the marker 40c is not particularly limited. Examples of the marker 40c shape include a circle, a triangle, a quadrangle, etc. In the embodiment shown in FIGS. 1 and 2, the marker 40c shape corresponds to a quadrangle (rectangle).

The size of the marker 40c is not particularly limited. For example, when the shape of the marker 40c corresponds to the quadrangle, it is preferable that a length of one side of the marker 40c is in a range of 1 to 4 mm. When the length of the one side is 5 mm or more, the size of the marker 40c increases with respect to a size of the puncture site P, and thus it is difficult to position a central portion of the inflatable portion 40 at the puncture site P.

The material of the marker 40c is not particularly limited. Examples of suitable marker 40c materials include an oily coloring agent such as ink, a resin kneaded with a pigment, etc.

The color of the marker 40c is not particularly limited when the color allows the inflatable portion 40 to be positioned at the puncture site P. However, a green-based color is preferable. When a green-based color is adopted, it is easy to visually recognize the marker 40c on blood or skin, and thus the inflatable portion 40 is more easily positioned in the puncture site P.

The marker 40c is preferably translucent or colored transparent. In this way, the puncture site P may be visually recognized from the outer surface side of the marker 40c.

The method of providing the marker 40c on the inflatable portion 40 is not particularly limited. Examples include printing the marker 40c on the inflatable portion 40, welding the marker 40c to the inflatable portion 40, applying an adhesive to one surface of the marker 40c to paste the marker 40c to the inflatable portion 40, etc.

Figure 4:
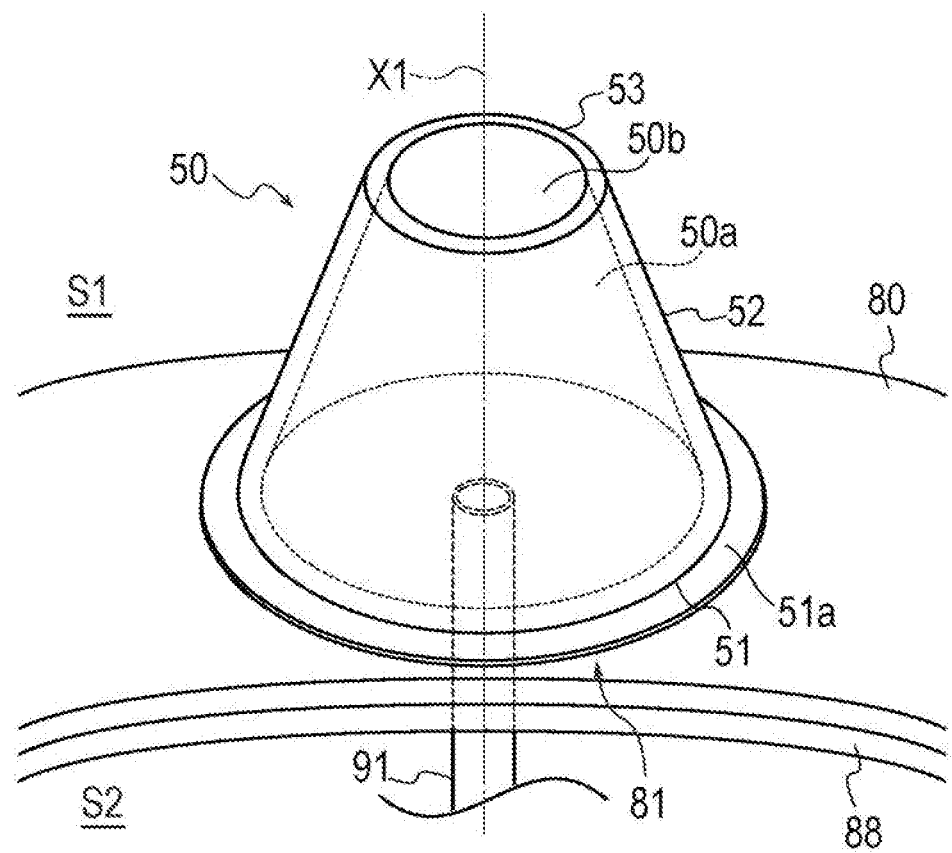
FIG. 4 is a schematic perspective view illustrating an injection part of the hemostatic device according to the embodiment shown in FIG. 1.

The injection part 50 has a function of injecting air (i.e., is configured to inject air) into the inflatable portion 40. As illustrated in FIG. 3 and FIG. 4, the injection part 50 is formed of a three-dimensional (3D) member including a housing space 50a capable of housing air.

Figure 5:
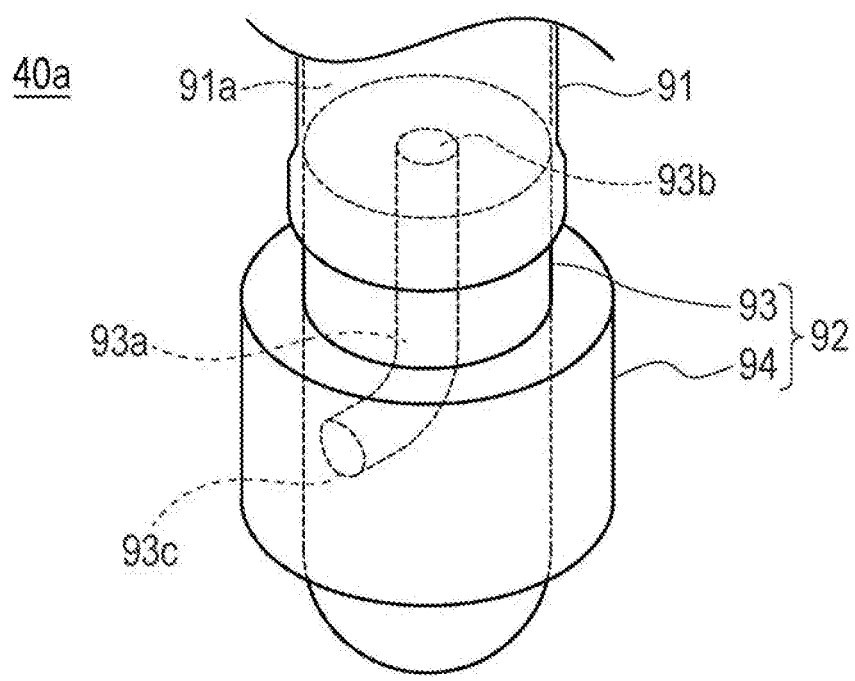
FIG. 5 is a schematic perspective view illustrating a backflow check structure of the hemostatic device according to the embodiment shown in FIG. 1.

As illustrated in FIG. 4 and FIG. 5, the injection part 50 has a hole portion 50b (an open hole or aperture) that penetrates the injection part 50 and communicates with the housing space 50a. The hole portion 50b is disposed on a perpendicular line X1 with respect to a region of the second support plate 80 in which the injection part 50 is disposed. In the present embodiment, the region of the second support plate 80 in which the injection part 50 is disposed is close to the central portion 81 of the second support plate 80.

The injection part 50 includes a bottom part 51 secured to the second support plate 80, a vertical wall part 52 projecting from the bottom part 51 toward the hole portion 50b, and an upper part 53 including the hole portion 50b. The bottom part 51 is provided with a securing portion 51a secured with the injection part 50 on the second support plate 80. For example, the injection part 50 may be secured to the second support plate 80 by an adhesive, etc.

In the embodiment shown in FIG. 4, the bottom part 51 of the injection part 50 is formed by an opening directly facing an outer surface of the second support plate 80. For this reason, the bottom part 51 is not included in a bottom face of the injection part 50, and a part of the outer surface of the second support plate 80 is included in the bottom face of the injection part 50 (i.e., the bottom part 51 has a hole as shown in FIG. 4 such that part of the outer surface of the second support plate 80 serves as the bottom surface of the injection part 50). The housing space 50a of the injection part 50 corresponds to a space surrounded by this part of the outer surface of the second support plate 80 and the interior surface of the vertical wall part 52.

An outer periphery of the vertical wall part 52 is formed to become smaller from the bottom part 51 side to the hole portion 50b side (a direction away protruding from the bottom part 51). As illustrated in FIG. 4 and FIG. 9, the vertical wall part 52 is formed in a tapered shape in a cross section parallel to the perpendicular line X1 with respect to the region of the second support plate 80 in which the injection part 50 is disposed. The tapered shape mentioned herein means a shape in which an outer peripheral dimension gradually decreases from the bottom part 51 toward the hole portion 50b toward the perpendicular line X1 passing through a center position of the hole portion 50b in plan view.

The external shape of the injection part 50 is not particularly limited and may correspond to, for example, a polygonal prism such as a quadrangular prism, a sphere having no distinction between the bottom part, the vertical wall part, and the upper part, a shape other than a tapered shape in section view, etc. Even though the injection part 50 is illustrated in which the bottom part 51 and the upper part 53 include openings (hole portions), the injection part 50 may have a structure in some embodiments in which a bottom face is formed in the bottom part and an upper face is formed in the upper part. In addition, the number of hole portions is not particularly limited as long as there is at least one or more hole portion. The shape of the hole portion(s) is not limited to the illustrated shape.

The volume of the housing space 50a of the injection part 50 is preferably about ¼ to ⅓ of the volume of the inflatable space 40a of the inflatable portion 40. The injection part 50 is thus formed to an appropriate size to help prevent the injection part 50 from hindering manipulation, etc. performed around the hemostatic device 10. It is also possible to reduce the number of times of performing an injection operation of injecting air into the inflatable portion 40 described below.

The injection part 50 is preferably made of, for example, an elastomer material such as silicone rubber or latex rubber, a thermoplastic plastic material such as polypropylene or polyethylene, or various thermoplastic elastomer materials having both properties of these materials so that the injection part 50 is contractible and can be restored (is restorable) to an original shape after contraction.

The housing space 50a of the injection part 50 communicates with the inflatable space 40a of the inflatable portion 40 through the tube 91 as illustrated in FIG. 8.

The injection part 50 obtains an initial shape illustrated in FIG. 4 by taking air into the housing space 50a from the hole portion 50b (i.e., when the hole portion 50b is uncovered, air enters the housing space 50a so that the injection part 50 takes the initial shape shown in FIG. 4). When an operation of inflating the inflatable portion 40 using the injection part 50 is performed, the injection part 50 is deformed while the hole portion 50b is blocked by a finger F1 (of an operator) as illustrated in FIG. 8.

When an operation of deforming the injection part 50 is performed as described above, air is sent to the inflatable portion 40 via the tube 91. When an operation of sending air to the inflatable portion 40 is to be performed again, the finger F1 is moved away from the hole portion 50b (to uncover the hole portion 50b) so that the housing space 50a communicates with the outside. The injection part 50 is thus restored to the initial shape illustrated in FIG. 9 by air taken into the housing space 50a from the hole portion 50b. When the injection part 50 is deformed again after air is taken into the housing space 50a, the air may be sent (conveyed) to the inflatable portion 40.

The injection part 50 extends in a direction away from the outer surface of the second support plate 80, and the hole portion 50b is disposed on the perpendicular line X1 with respect to the region of the second support plate 80 in which the injection part 50 is disposed. The pressing direction of the injection part 50 when air is injected into the inflatable portion 40 thus corresponds to a direction (vertical direction) along the perpendicular line X1 with respect to the region of the second support plate 80 in which the injection part 50 is disposed (see FIG. 4). It is thus possible to efficiently apply a force to the injection part 50 by a finger F1 and to smoothly send air to the inflatable portion 40 (i.e., inflate the inflatable portion 40 with air). In addition, the injection part 50 rarely buckles on the bottom part 51 side during the pressing operation to deform the injection part 50 because the outer periphery of the vertical wall part 52 becomes smaller from the bottom part 51 side toward the hole portion 50b side. It is thus possible to prevent damage (or undesirable deformations) to the injection part 50 such as folding from occurring. Further, since the outer periphery of the vertical wall part 52 becomes smaller from the bottom part 51 side toward the hole portion 50b side, the injection part 50 is transformed during the pressing operation such that the hole portion 50b side of the injection part 50 is folded to (moved towards) the inside of the housing space 50a of the injection part 50. For this reason, it is possible to deform the injection part 50 from the hole portion 50b side toward the bottom part 51 side with a small force, and to efficiently send air in the housing space 50a to the inflatable portion 40.

It is possible to help prevent the second support plate 80 from being transformed during the pressing operations to inflate the inflatable portion 40 because the injection part 50 is secured on the relatively rigid second support plate 80. In addition, since the second support plate 80 is rotatably connected to the first support plate 70, a pressing force transmitted to the second support plate 80 at the time of pressing the injection part 50 is absorbed by a connecting part between the second support plate 80 and the first support plate 70. As a result, a pressing force generated when the injection part 50 is pressed is suppressed from being transmitted to the first support plate 70 and is suppressed from being transmitted to the puncture site P. The wearer of the hemostatic device 10 can thus appropriately detect only a pressing force applied to the puncture site P from the inflatable portion 40 while an operation of inflating the inflatable portion 40 is performed. Therefore, when the injection part 50 is operated based on a pressing force felt by the wearer, it is possible to inject an optimum amount of air for hemostasis in the puncture site P into the inflatable portion 40.

The injection part 50 is disposed on an outer surface side of the first support plate 70. When the hemostatic device 10 is mounted on the wrist W, the hole portion 50b of the injection part 50 is directed to a side in a direction in which the palm faces and diagonally outward of the wrist W as shown in FIGS. 1 and 7. Normally, the doctor, etc. performs an operation with respect to the hemostatic device 10 from the outer surface side (left and right sides of FIG. 7) of the wrist W parallel to the direction of the palm. The hole portion 50b of the injection part 50 is rarely blocked by an article, etc. present in the surroundings while the operation with respect to the hemostatic device 10 is performed, and the wearer, the doctor, etc. may relatively easily visually verify whether the hole portion 50b is in a blocked state. The wearer may relatively easily visually verify whether the hole portion 50b is in the blocked state (e.g., when the wearer is in a hospital room after the operation with the hemostatic device 10 is completed). The hemostatic device 10 can thus prevent the injection part 50 from being deformed while the hole portion 50b is blocked with the surrounding article, etc., and prevent the puncture site P from being pressed more than necessary. In addition, when the hemostatic device 10 is mounted on the right hand wrist W as illustrated in FIG. 1 and FIG. 7, it is possible to prevent a pressing force from being applied to an ulnar artery at the time of pressing the injection part 50.

The first support plate 70 and the second support plate 80 are disposed on the long axis A1 of the band 20, and the injection part 50 is disposed on the second support plate 80 as shown in FIGS. 2 and 3. The injection part 50 thus rarely comes into contact with the wrist W of the wearer compared to when the injection part 50 is provided to protrude from the band 20 toward the wrist W side. Therefore, discomfort felt by the wearer can be reduced. The injection part 50 is disposed on the second support plate 80 (which is a different member from the first support plate 70 on which the inflatable portion 40 is disposed) and thus does not hinder positioning of the inflatable portion 40 to the puncture site P performed using the marker 40c.

As illustrated in FIG. 3 and FIG. 4, a proximal portion of the tube 91 is attached to the bottom part 51 side of the injection part 50, and a distal portion of the tube 91 is attached to the inflatable portion 40 so that air in the tube 91 may enter the inflatable space 40a of the inflatable portion 40. The position at which the tube 91 is attached in the injection part 50 is not particularly limited as long as communication is allowed between the housing space 50a of the injection part 50 and the inflatable space 40a of the inflatable portion 40 (i.e., the tube 91 connects the housing space 50a to the inflatable space 40a so that the spaces 50a, 40a can communicate with one another). For example, the proximal portion of the tube 91 may be attached to the vertical wall part 52 of the injection part 50 (i.e., the inner surface of the vertical wall part 52). However, when the hole portion 50b is disposed on the upper part 53 side as in the embodiment shown in FIG. 4, the proximal portion of the tube 91 is preferably attached to the bottom part 51 side of the injection part 50 to efficiently send air in the housing space 50a to the inflatable portion 40.

A through-hole is provided in the second support plate 80 as shown in FIG. 3. The proximal portion of the tube 91 is disposed to be inserted into the through-hole. A through-hole into which the tube 91 is inserted is similarly provided in the auxiliary pressing portion 78. In addition, a through-hole 76 is provided in the first protrusion 75a of the first support plate 70 allowing a part of the tube 91 to be inserted therethrough. The tube 91 is thus connected to the inflatable portion 40 through the through-hole of the band 20, the through-hole of the auxiliary pressing portion 78, an inner surface side of the second support plate 80, and the through-hole 76. This configuration helps make it is possible to prevent an external force from being inadvertently applied to the tube 91 when the hemostatic device 10 is mounted on the wrist W or detached from the wrist W, and to prevent damage, etc. to the tube 91 from occurring. To prevent damage, etc. to the tube 91 from occurring, for example, a part of the tube 91 may be disposed inside the first support plate 70 or inside the second support plate 80. However, disposition (arrangement) of the tube 91 is not particularly limited. For example, the tube 91 may be disposed to go around the outer surface side of the second support plate 80 without providing a through-hole in the second support plate 80.

As illustrated in FIG. 5, a backflow check structure 92 is provided at the distal portion of the tube 91 disposed in the inflatable space 40a to prevent backflow from the inside of the inflatable space 40a to the injection part 50 side.

The backflow check structure 92 is positioned inside the inflatable portion 40. As illustrated in FIG. 5, the backflow check structure 92 includes a core material 93 connected to the distal portion of the tube 91 and a covering member 94 covering the core material 93.

The core material 93 is connected to the tube 91 by inserting and securing a proximal portion of the core material 93 into a distal side of a lumen 91a of the tube 91.

The core material 93 has a substantially columnar external shape. The core material 93 includes a proximal end opening 93b that opens inside the lumen 91a of the tube 91, a distal end opening 93c that opens on a surface on which the covering member 94 is provided in the core material 93, and a lumen 93a that communicates with the proximal end opening 93b and the distal end opening 93c.

The core material 93 may be connected to the tube 91 in a different method than inserting and securing the proximal portion of the core material 93 into the lumen 91a of the tube 91. For example, each of a distal end surface of the core material 93 and a proximal end surface of the tube 91 may be secured in a butted (abutting) state, and the lumen 93a of the core material 93 and the lumen 91a of the tube 91 may be allowed to airtightly communicate with each other.

The core material 93 material preferably has a higher hardness than that the hardness of the covering member 94. Examples of such a material (for the core material 93) include a known metal material, a plastic material, etc.

The covering member 94 has a cylindrical external shape. The core material 93 is inserted into the covering member 94.

The covering member 94 material preferably corresponds to an elastic member. Examples of such a material include an elastomer material such as butyl rubber, polysulfide rubber, epichlorohydrin rubber, high nitrile rubber, fluororubber, or silicone rubber, various thermoplastic elastomer materials, etc.

Figure 6A:
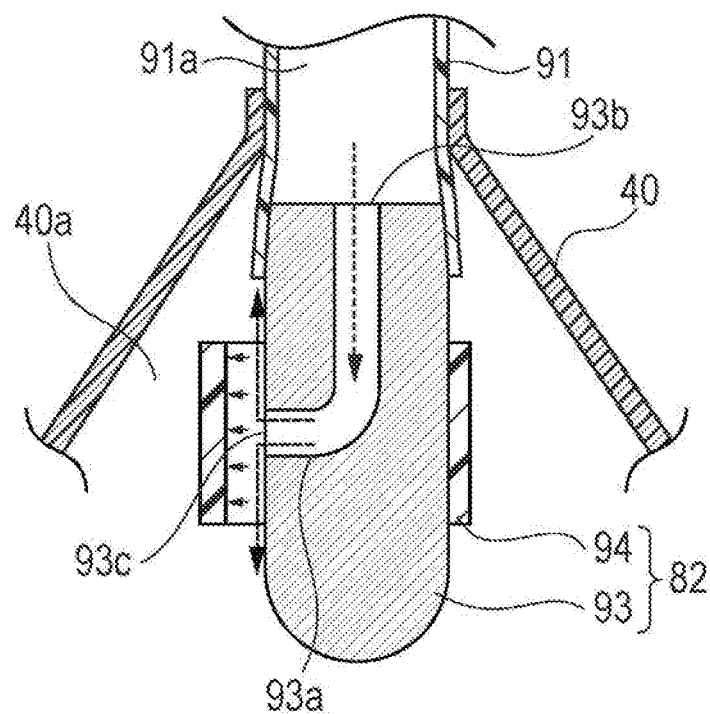
FIGS. 6A and 6B depict enlarged cross-sectional views illustrating the backflow check structure of the hemostatic device according to the embodiment of FIG. 1.
Figure 6B:
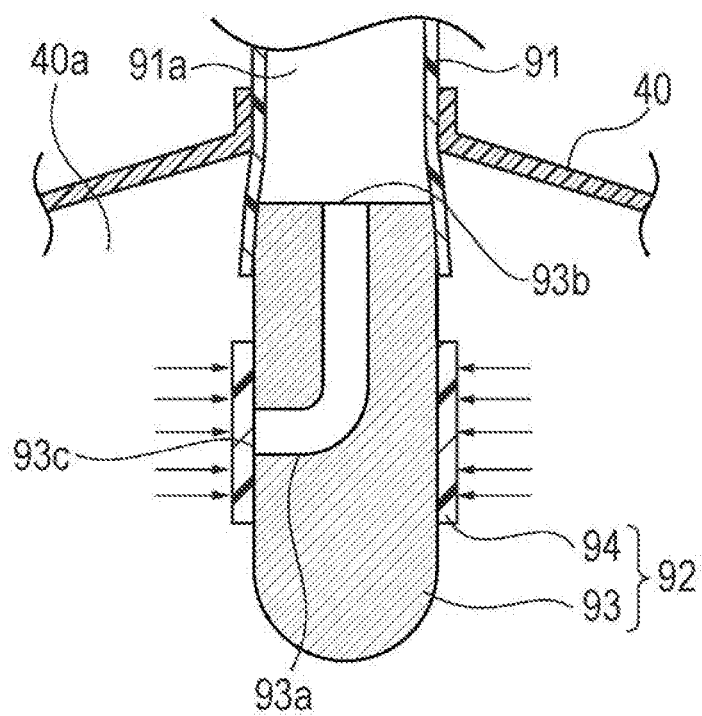

An operation of the backflow check structure 92 will be described with reference to FIGS. 6A and 6B. In FIGS. 6A and 6B, the dotted arrows indicate a flow of air, and the solid arrows indicate a direction of the pressure applied to the covering member 94 by air.

As illustrated in FIG. 6A, when air is injected into the tube 91 from the injection part 50 in a state in which the inflatable portion 40 is insufficiently inflated, air passes through the lumen 93a of the core material 93 to apply a pressure in a direction away from the core material 93 to the covering member 94.

The covering member 94 is separated from an outer surface of the core material 93 to allow communication between the distal end opening 93c and the inflatable space 40a when the air pressure received from the injection part 50 is greater than or equal to a predetermined magnitude. For example, when an operation of sufficiently deforming the injection part 50 is not performed, and the amount of air sent from the injection part 50 is relatively small, the pressure applied to the covering member 94 is relatively lower, and thus the distal end opening 93c does not communicate with the inflatable space 40a (because the pressure applied is not great enough to cause the covering member 94 to open). On the other hand, when the injection part 50 is slowly pressed for a relatively long time, and the operation of sufficiently deforming the injection part 50 is performed, the covering member 94 is separated from the outer surface of the core material 93. Even if the hole portion 50b of the injection part 50 is erroneously closed by an article, etc., air is not inadvertently sent into the inflatable portion 40 when the injection part 50 is not sufficiently deformed, and thus it is possible to suitably prevent the puncture site P from being pressed more than necessary.

As illustrated in FIG. 6B, when the inflatable portion 40 is sufficiently inflated, air in the inflatable portion 40 applies pressure in a direction of coming into contact with the core material 93 to the covering member 94 (i.e., pressure on the outer surface of the covering member 94 to urge the covering member 94 toward the core material as shown in FIG. 6B). The distal end opening 93c is thereby blocked by the covering member 94, and thus the air in the inflatable portion 40 does not flow back to the injection part 50. In addition, the air in the inflatable portion 40 applies a pressure to the covering member 94 to block the distal end opening 93c when the inflatable portion 40 is sufficiently inflated. The pressure is higher than the injection pressure of air (i.e., the pressure of the air received from the injection part 50). Therefore, when the inflatable portion 40 is sufficiently inflated and the internal pressure of the inflatable portion 40 becomes a predetermined value, air may not be injected from the injection part 50 into the inflatable portion 40. It is thus possible to advantageously prevent air from being injected into the inflatable portion 40 more than necessary (i.e., after the inflatable portion 40 is sufficiently inflated) and prevent the inflatable portion 40 from excessively inflating, which would press the puncture site P more than necessary.

Next, a description will be given of a use example of the hemostatic device 10 according to the present embodiment.

Before the hemostatic device 10 is mounted on the wrist W, the inflatable portion 40 is in a state of not being inflated (i.e., deflated) as illustrated in FIG. 2. As illustrated in FIG. 7 and FIG. 8, when the radial artery R of the right hand wrist W is punctured, the puncture site P is at a position biased to a thumb side. Normally, the introducer sheath is indwelled in the puncture site P. The band 20 is wrapped around the wrist W (in which the introducer sheath is indwelled), and the inflatable portion 40 and the band 20 are positioned such that the marker 40c on the inflatable portion 40 overlaps the puncture site P. The respective female sides 31a and 31b and the male side 32 of the surface fastener 30 are brought into contact with each other and joined to each other, thereby mounting the band 20 on the wrist W.

After the hemostatic device 10 is mounted on the wrist W, the injection part 50 is deformed while the hole portion 50b of the injection part 50 is blocked with the finger F1 as shown in FIG. 8. This causes the air in the injection part 50 to be injected into the inflatable portion 40, and the inflatable portion 40 is inflated (e.g., shown in the progression of FIGS. 8 and 9). Since the inflatable portion 40 can be inflated by the injection part 50 integrated with the inflatable portion 40, a doctor or a nurse does not need to carry a separate dedicated instrument (syringe, etc.) for inflating the inflatable portion 40.

After the inflatable portion 40 is inflated, the introducer sheath is withdrawn from the puncture site P. As illustrated in FIG. 9, the inflatable portion 40 after inflation applies a pressing force to the puncture site P.

Figure 10:
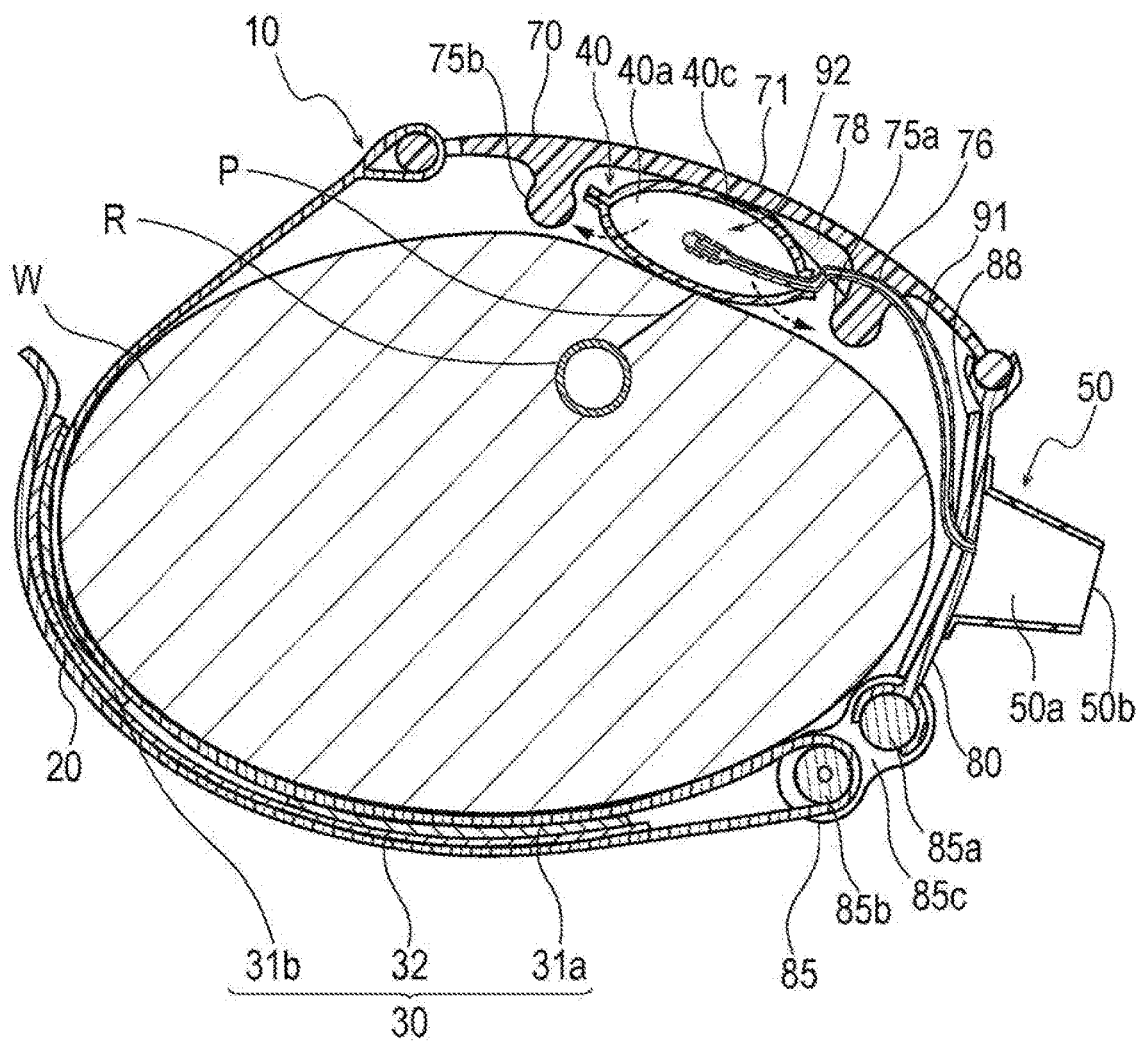
FIG. 10 is a cross-sectional view taken along VIII-VIII line of FIG. 7, and is a diagram illustrating a state in which the inflatable portion is contracted.

After the inflatable portion 40 is inflated, as indicated by an arrow in FIG. 10, gas in the inflatable portion 40 is discharged to the outside of the inflatable portion 40 over time to an extent that vascular occlusion can be prevented while a pressing force is applied to the puncture site P as shown in FIG. 10 (air flow indicated by the dotted line arrows of FIG. 10). Gas in the inflatable portion 40 is able to be discharged to the outside of the inflatable portion 40 due to the inflatable portion 40 material being a thermosetting elastomer as described above. The doctor, the nurse, etc. may eliminate an effort to perform an operation of depressurizing the inflatable portion 40 according to a degree of hemostasis based on this configuration.

When hemostasis is insufficiently performed after inflation of the inflatable portion 40, air may be injected into the inflatable portion 40 again to raise the internal pressure of the inflatable portion 40. For example, when it is desired to return the internal pressure of the inflatable portion 40 to the internal pressure at the time of injecting air into the inflatable portion 40, air discharged from the inflatable portion 40 may be injected.

When a predetermined time elapses, and hemostasis in the puncture site P is completed, the hemostatic device 10 is removed from the wrist W. The hemostatic device 10 is removed from the wrist W by peeling off the respective female sides 31a and 31b and the male side 32 of the surface fastener 30.

As described above, the hemostatic device 10 according to the present embodiment includes the band 20 for wrapping around the wrist W, the means for securing 30 that secures the band 20 in a state of being wrapped around the wrist W, the inflatable portion 40 that is inflated by injection of air to press the puncture site P, the injection part 50 that has the housing space 50a capable of housing air and can inject air housed in the housing space 50a into the inflatable portion 40, and the support plate 60 connected to the band 20. The support plate 60 includes the first support plate 70 and the second support plate 80 which are disposed on the long axis A1 of the band 20 (i.e., spaced apart from one another in the longitudinal direction of the band). The inflatable portion 40 is disposed on the first support plate 70 and the second support plate 80 is movably connected to the first support plate 70. The injection part 50 includes the hole portion 50b penetrating the injection part 50 and communicating with the housing space 50a and is disposed on the second support plate 80.

According to the hemostatic device 10 configured as described above, air is injected into the inflatable portion 40 by the injection part 50, which communicates with the inflatable portion 40. The doctor or the nurse can thus inflate the inflatable portion 40 without using a separate dedicated instrument. In addition, the injection part 50 is disposed on the second support plate 80 and rarely comes into contact with the wrist W (i.e. is specifically positioned to avoid contacting the wrist W). Thus, it is possible to reduce discomfort felt by the wearer. The injection part 50 is disposed on the second support plate 80 at a different position from that of the first support plate 70 on which the inflatable portion 40 is disposed, and the second support plate 80 is movably disposed with respect to the first support plate 70. Transmission of an inadvertent force from the injection part 50 to the puncture site P at the time of sending air from the injection part 50 to the inflatable portion 40 can thereby be suppressed. By integrally providing the hemostatic device 10 and the injection part 50 for injecting air in the above-described configuration, the hemostatic device 10 may reduce a labor of an operator and suppress transmission of an inadvertent force to a puncture site P of a patient.

The injection part 50 has the bottom part 51 disposed on the second support plate 80 and the vertical wall part 52 projecting upward from the bottom part 51 toward the hole portion 50b. The outer periphery (outer diameter) of the vertical wall part 52 gradually decreases (tapers) from the bottom part 51 to the upper part 53 of the injection part 50. The injection part 50 may thus help prevent damage (such as folding) from occurring on the bottom part 51 side.

The vertical wall part 52 of the injection part 50 is formed in a tapered shape in a cross section parallel to the perpendicular line X1 with respect to the region of the second support plate 80 in which the injection part 50 is disposed. It is thus possible to smoothly send air from the upper part 53 side of the injection part 50 toward the bottom part 51 side and further from the bottom part 51 side toward the inflatable portion 40 when the injection part 50 is deformed by an operator pressing down on the upper part 53 of the injection part 50, e.g., with their finger F1.

The hole portion 50b (a thru-hole) of the injection part 50 is disposed on the perpendicular line X1 with respect to the region of the second support plate 80 in which the injection part 50 is disposed. The injection part 50 is thus pressed inward (toward the wrist W) in a vertical direction along the perpendicular line X1 when air is injected into the inflatable portion 40. As a result, it is possible to efficiently apply a force to the injection part 50 from the finger F1 and to smoothly send air to the inflatable portion 40.

The first support plate 70 and the second support plate 80 are made of a material more rigid than that of the band 20. For this reason, it is possible to suppress inflation of the inflatable portion 40 in the direction away from the body surface of the wrist W when the inflatable portion 40 is inflated. Therefore, the inflatable portion 40 may suitably press the puncture site P. Further, it is possible to suppress transformation of the second support plate 80 when the injection part 50 disposed on the second support plate 80 is pressed and to prevent an unnecessary pressing force from being applied from the second support plate 80 to the wrist W.

The second support plate 80 has the first surface on which the injection part 50 is disposed and the second surface opposing the first surface. The cushioning member 88 that alleviates a contact force (pressing force) transmitted from the second surface of the second support plate 80 to the wrist W is disposed on the second surface. The cushioning member 88 prevents the second support plate 80 from being pressed against the wrist W to give discomfort to the wearer while pressure hemostasis is performed in a state in which the hemostatic device 10 is mounted on the wrist W.

The hemostatic device 10 has the tube 91 that communicates between the inflatable portion 40 and the injection part 50, and the first support plate 70 has the first protrusion 75a disposed on the second support plate 80 side and the second protrusion 75b disposed on the band 20 side and formed to interpose the inflatable portion 40 between the first protrusion 75a and the second protrusion 75b along the direction of the long axis A1 of the band 20. The tube 91 penetrates through the first protrusion 75a. The first protrusion 75a and the second protrusion 75b can keep the distance between the inflatable portion 40 and the puncture site P before start of inflation at a predetermined distance irrespective of a difference in outer periphery dimension of the wrist W for each wearer, and apply a certain pressing force regardless of the wearer. Since the tube 91 is connected to the inflatable portion 40 by penetrating the first protrusion 75a, it is possible to prevent an external force from being inadvertently applied to the tube 91 and prevent damage, etc. to the tube 91 from occurring at the time of mounting the hemostatic device 10 on the wrist W or at the time of detaching the hemostatic device 10 from the wrist W.

The first support plate 70 has the auxiliary pressing portion 78 disposed on the second protrusion 75b side of the first protrusion 75a to adjust a pressing direction of the inflatable portion 40 in an inflated state. The pressing force can be efficiently applied to the puncture site P because the pressing direction of the inflatable portion 40 is adjusted to be directed to the puncture site P by the auxiliary pressing portion 78 when the inflatable portion 40 is inflated.

The second support plate 80 has the connecting member 85 movably connected to the band 20. The connecting member 85 connects the band 20 and the second support plate 80 to each other at the time of mounting the hemostatic device 10 on the wrist W and allows adjustment of the band 20 length according to the outer periphery length of the wrist W of the wearer. In this way, the magnitude of the outer periphery length of the wrist W of the wearer does not limit the use of the hemostatic device 10.

Next, modifications of the embodiment shown in FIGS. 1-6 will be described. Note that in description of each modification, the same reference symbol will be assigned to the same configuration as that of the embodiment, and a description thereof will be omitted (i.e., the components that are the same as described above have the same reference numerals on the drawings and a description thereof is not repeated).

(Modification 1)

Figure 11:
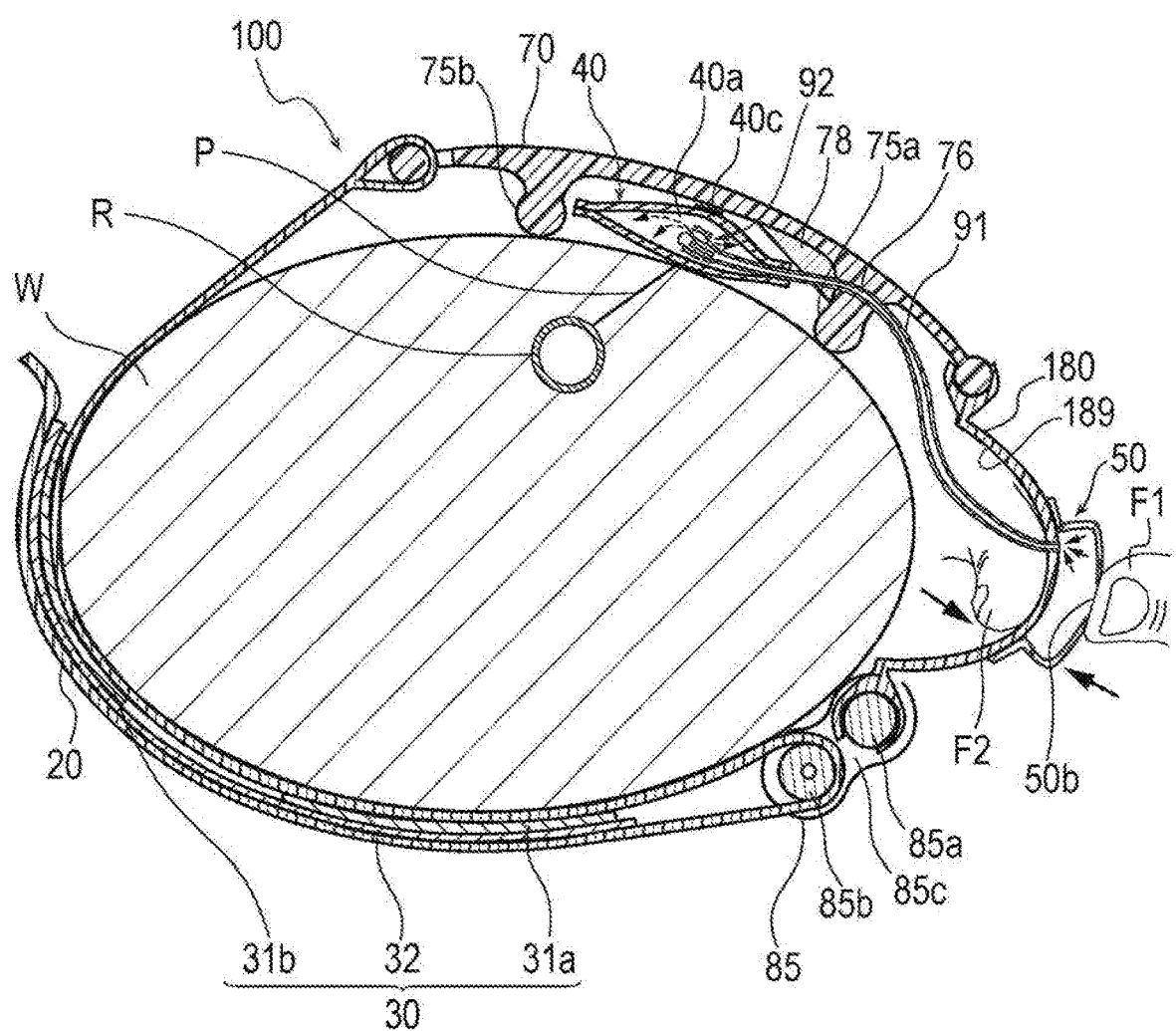
FIG. 11 is a cross-sectional view illustrating a use example of a hemostatic device according to Modification 1 of the embodiment.

FIG. 11 is a diagram for description of a hemostatic device 100 according to Modification 1.

In the hemostatic device 100 according to Modification 1, a configuration of a second support plate 180 is different from that of the embodiment shown in FIGS. 1-6. The second support plate 180 is formed to create a recess 189 (i.e., a space) between the wrist W and the second support plate 180 when the band 20 is wrapped around and secured to the wrist W.

The second support plate 180 is curved to protrude from an inner surface side to an outer surface side of the second support plate 180 (i.e., the second support plate 180 is convex and protrudes outward relative to the wrist W to create the recess 189). The recess 189 recessed from the inner surface side to the outer surface side of the second support plate 180 is formed on the inner surface side of the second support plate 180 as shown in FIG. 11.

The recess 189 is formed to have a size for partitioning a space into which a finger F2 can be inserted between the wrist W and the second support plate 180. Note that a cross-sectional shape, the size, etc. of the recess 189 are not particularly limited, and may be appropriately modified.

The injection part 50 is attached to an outer surface side of a part of the second support plate 180 in which the recess 189 is provided.

The inflating of the inflatable portion 40 of the hemostatic device 100 is next described. First, a finger (for example, an index finger) F2 is inserted into the recess 189 and the hole portion 50b provided on the upper face of the injection part 50 is blocked with another finger (for example, a thumb) F1. Then, the injection part 50 is deformed by the operator bringing one finger F1 towards the second support plate 80 while supporting the second support plate 80 by the other finger F2. By this operation, air is injected into the inflatable portion 40.

A member (for example, a lubricant-coated sheet-shaped member) for reducing friction acting between the finger F2 inserted into the recess 189 and the wrist W may be disposed between the finger F2 and the wrist W. In addition, a cushioning member may be disposed in a part that may come into contact with the wrist W in the vicinity of an inner surface of the recess 189.

According to the hemostatic device 100 according to Modification 1, the second support plate 180 has the recess 189 that forms a space between the wrist W and the second support plate 180 when the wrist W is wrapped around and secured to the band 20. Therefore, it is possible to deform the injection part 50 by one finger F1 while supporting the second support plate 180 by another finger F2. In this way, a pressing force applied when one finger F1 deforms the injection part 50 is less likely to be transmitted to the puncture site P. In addition, since the injection part 50 can be deformed by pinching the injection part 50 with the two fingers F1 and F2, it is possible to easily and smoothly inject air.

(Modification 2)

Figure 12:
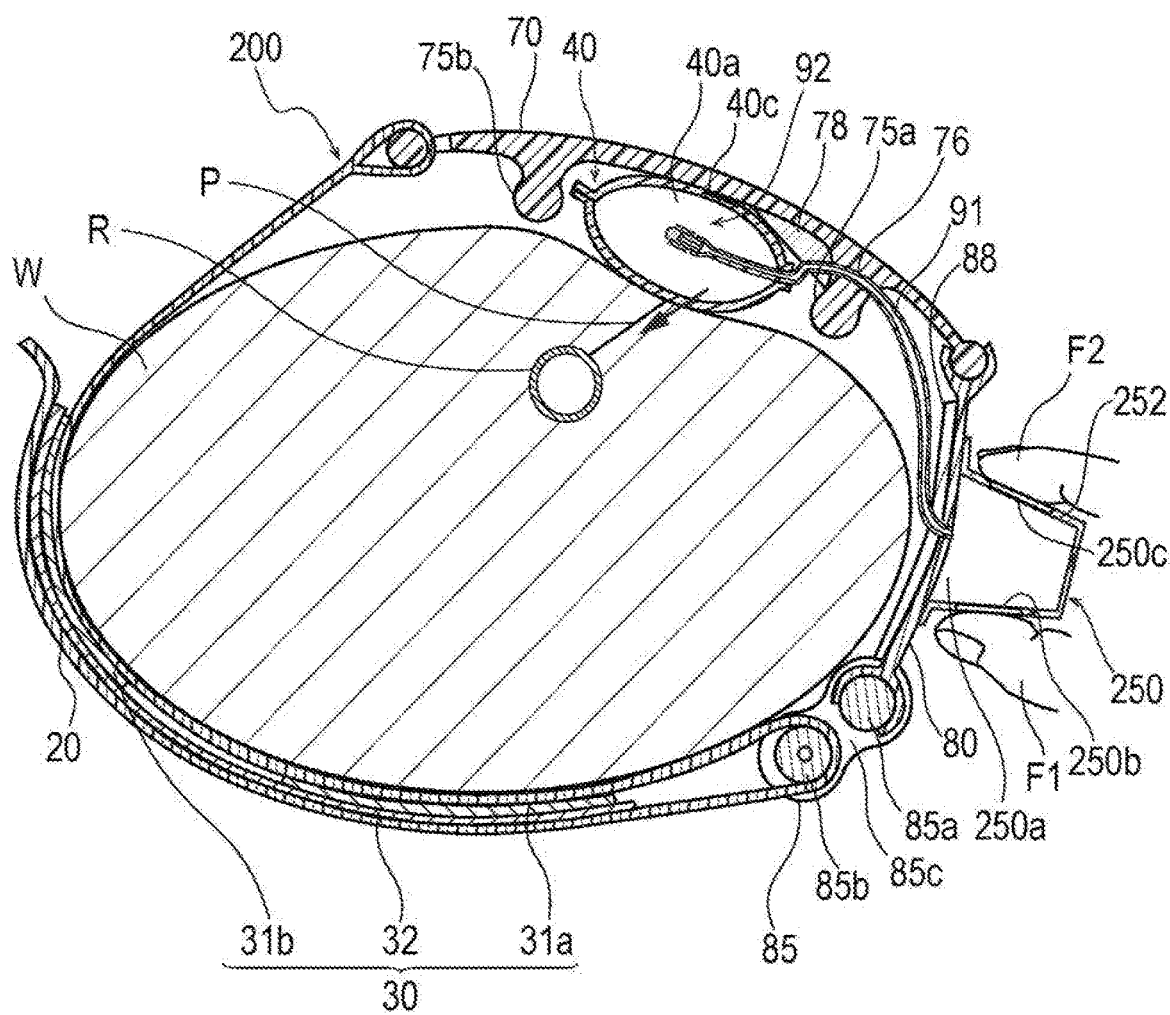
FIG. 12 is a cross-sectional view illustrating a use example of a hemostatic device according to Modification 2 of the embodiment.

FIG. 12 is a diagram for description of a hemostatic device 200 according to Modification 2.

The hemostatic device 200 according to Modification 2 is different from that of the embodiments described above in that two hole portions 250*b* and 250*c* are provided in a vertical wall part 252 of an injection part 250. Air can be inducted into the housing space 250*a* of the injection part 250 through the two hole portions 250*b* and 250*c* (i.e., open holes or thru-holes).

The two hole portions 250*b* and 250*c* penetrate the vertical wall part 252 in a thickness direction (a transverse direction intersecting the protruding direction of the vertical wall part 252) are provided in the vertical wall part 252. The two hole portions 250*b* and 250*c* are provided to face each other. The cross-sectional shape, a material, a structure, etc. of the injection part 250 may be configured similarly to the injection part 50 according to the embodiments described above.

The hole portions 250*b* and 250*c* are blocked with two fingers F1 and F2, respectively, and the fingers F1 and F2 are moved toward one another to inflate the inflatable portion 40. In this way, the injection part 250 is deformed and contracted, and air is injected into the inflatable portion 40.

According to the hemostatic device 200 according to Modification 2, the hole portions 250*b* and 250*c* are provided in the vertical wall part 252 of the injection part 250. The pressing force for deforming the injection part 250 thus acts in a transverse direction intersecting a direction from the injection part 250 to the wrist W. Therefore, it is possible to more favorably prevent a situation in which the puncture site P is pressed more than necessary by an injection operation of injecting air into the inflatable portion 40.

In addition, the two hole portions 250*b* and 250*c* are provided at positions facing each other. For this reason, it is possible to relatively easily close the hole portions 250*b* and 250*c* using two fingers F1 and F2, and to relatively easily inject air into the inflatable portion 40. In addition, even when one hole portion comes into contact with a surrounding article, etc. and blocked, a possibility that the other hole portion will also be blocked becomes low. For this reason, even when the injection part 250 is unintentionally deformed, the injection part 250 has a low possibility of (inadvertently) injecting air into the inflatable portion 40.

(Modification 3)

Figure 13:
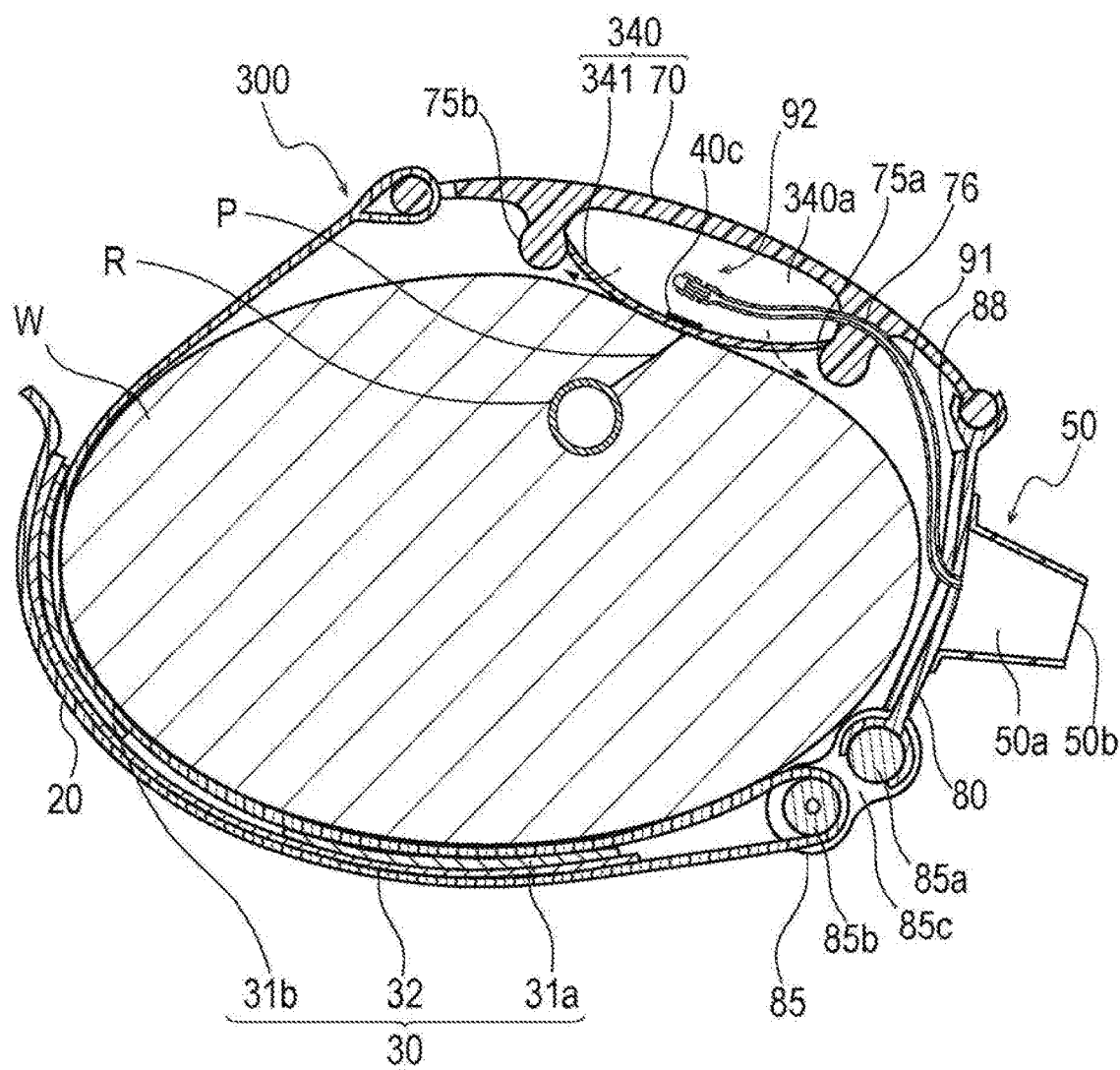
FIG. 13 is a cross-sectional view illustrating a use example of a hemostatic device according to Modification 3 of the embodiment.

FIG. 13 is a diagram for description of a hemostatic device 300 according to Modification 3.

The hemostatic device 300 according to Modification 3 is different from that of the embodiment in that an inflatable portion 340 includes the first support plate 70 and a membrane material 341 attached to the first support plate 70.

A peripheral portion of the membrane material 341 is joined to the inner surface side of the first support plate 70 so that the membrane material 341 is disposed between the first protrusion 75*a* and the second protrusion 75*b* of the first support plate 70. A space between the membrane material 341 and the first support plate 70 corresponds to an inflatable space 340*a* into which air is injected.

The distal portion of the tube 91 and the backflow check structure 92 are positioned in the inflatable space 340*a*. Air is thus injected into the inflatable space 340*a* when the injection part 50 is deformed/contracted, which causes the membrane material 341 to protrude toward the wrist W (that is, the inflatable portion 340 inflates). As a result, the puncture site P is pressed.

The marker 40*c* is provided on the inner surface in the inflatable portion 340 so as not to directly come into contact with the puncture site P.

For example, the same material as a constituent material (a sheet made of a thermosetting elastomer, a sheet made of a thermosetting elastomer and a thermoplastic material, etc.) of the inflatable portion 40 described above may be used for the membrane material 341.

According to the hemostatic device 300 according to Modification 3, the inflatable portion 340 is created by joining the peripheral portion of one membrane material 341 to the first support plate 70. The number of members included in the inflatable portion 340 is thus relatively small, and the manufacturing cost of the hemostatic device 300 may be made relatively inexpensive.

(Modification 4)

Figure 14:
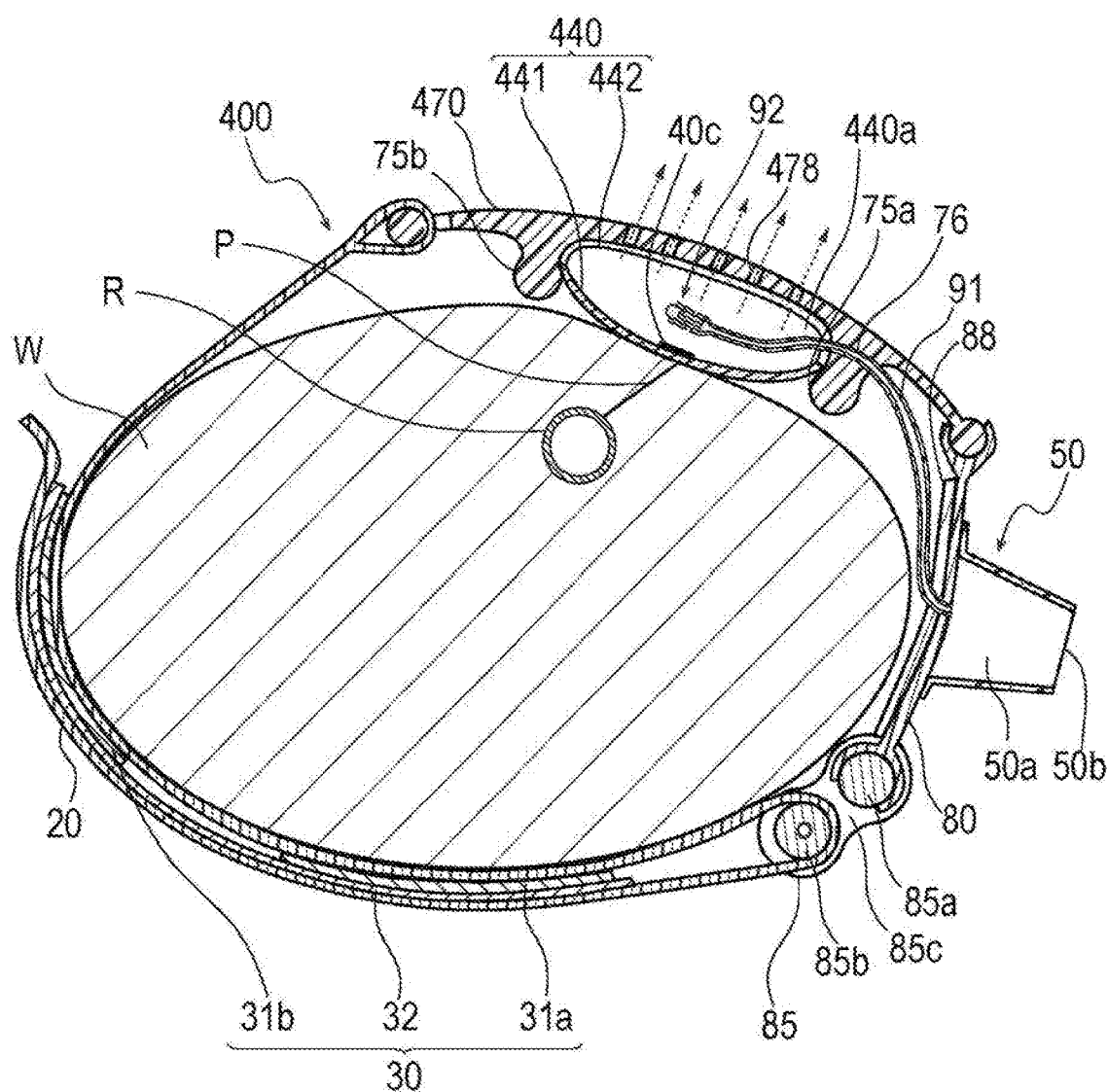
FIG. 14 is a cross-sectional view illustrating a use example of a hemostatic device according to Modification 4 of the embodiment.

FIG. 14 is a diagram for description of a hemostatic device 400 according to Modification 4.

The hemostatic device 400 according to Modification 4 is different from that of the embodiments described above in that air in an inflatable portion 440 is discharged over time from a permeable membrane 442 included in the inflatable portion 440 and an exhaust hole 478 provided in a first support plate 470.

The inflatable portion 440 includes a membrane material 441 disposed on the wrist W side. A permeable membrane 442, which has higher gas permeability than that of the membrane material 441, is disposed on the first support plate 470 side.

Peripheral portions of the membrane material 441 and the permeable membrane 442 are joined to each other in a state of being superimposed with each other. The permeable membrane 442 is attached to the inner surface of the first support plate 470 between the first protrusion 75*a* and the second protrusion 75*b* of the first support plate 470.

The membrane material 441 material is not particularly limited as long as the material has flexibility. Examples of the material include acrylic resins, polyvinyl chloride (particularly rigid polyvinyl chloride), polyolefins such as polyethylene, polypropylene and polybutadiene, polystyrene, poly(4-methyl pentene-1), polycarbonates, ABS resins, polymethyl methacrylate (PMMA), polyacetals, polyarylates, polyacrylonitriles, polyvinylidene fluorides, ionomers, acrylonitrile-butadiene-styrene copolymers, polyesters such as polyethylene terephthalate (PET) and polybutylene terephthalate (PBT), butadiene-styrene copolymers, aromatic or aliphatic polyamides, and fluorocarbon resins such as polytetrafluoroethylene.

The permeable membrane 442 material is not particularly limited as long as, for example, the material corresponds to a material or a structure in which a gas permeation amount is larger than that of the membrane material 441. Examples thereof include a single membrane using a thermosetting elastomer such as silicone or natural rubber, an asymmetric membrane using polyethylene, polyimide, cellulose, etc., and a particle-containing membrane containing fine particles for enhancing gas permeability into and out of the membrane.

The marker 40*c* is provided on an inner surface side of the inflatable portion 440 so as not to directly come into contact with the puncture site P.

A plurality of exhaust holes 478 penetrating the first support plate 470 in a thickness direction (i.e., thru-holes or apertures extending through the first support plate 470) is formed in a region of the first support plate 470 to which the permeable membrane 442 is attached.

According to the hemostatic device 400 according to Modification 4, air in the inflatable portion 440 is discharged over time (after inflation of the inflatable portion 440) from the permeable membrane 442 and the exhaust hole 478 provided in the first support plate 470. It is thus possible to reduce the pressing force acting on the puncture site P over time without an operation of the doctor or the nurse, and to suppress vascular occlusion, etc.

The peripheral portion of the membrane material 441 may not be joined to the peripheral portion of the permeable membrane 442, and may be, for example, directly joined to the first support plate 470. In this case, the peripheral portion of the membrane material 441 and the peripheral portion of the permeable membrane 442 may be separated from each other.

Even though the hemostatic device disclosed here has been described above through based on exemplary embodiments and modifications, the inventive hemostatic device is not limited only to the respective configurations described above, and can be appropriately modified based on the description of claims.

For example, each portion included in the hemostatic device may be replaced with a portion having an arbitrary configuration capable of exerting the same function. In addition, an arbitrary component may be added.

The hemostatic device is not limited to being mounted on the wrist, and may be used by being mounted on a leg, etc.

The description above illustrates a configuration in which the backflow check structure is provided in the inflatable portion. However, the position of the backflow check structure is not particularly limited as long as the backflow check structure is positioned between the inside of the inflatable portion and the injection part. In addition, the configuration of the backflow check structure may be appropriately changed depending on the arrangement position.

The description above illustrates a configuration in which gas (air) is discharged from the inflatable portion over time depending on the property of the constituent material of the inflatable portion. It is possible to adopt a configuration, however, that allows gas to be discharged, for example, using a well-known instrument (syringe, etc.), a gas discharging mechanism integrally provided on the hemostatic device, etc.

The structure of a part that connects the band and the first support plate, the structure of a part that connects the band and the second support plate, and the structure of a part that connects the first support plate and the second support plate are not limited to any particular structures described above. As long as at least the second support plate is movably connected to the first support plate, the structure of connecting respective members may be changed. A movable structure of the first support plate and the second support plate is also not limited to a structure in which both the support plates rotate, and it is sufficient that one member is movable relative to the other member.

The detailed description above describes a hemostatic device and a method for using the hemostatic device. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A hemostatic device comprising:
   a band configured to be wrapped around a limb of a living body at a site of the living body where bleeding is to be stopped, the band possessing a longitudinal direction;
   means for securing the band to the limb in a wrapped state;
   an inflatable portion comprising an interior, the inflatable portion being inflated by injection of gas into the interior to expand the inflatable portion and cause the inflatable portion to press the site where bleeding is to be stopped;
   an injection part comprising a housing space configured to house gas, the injection part being configured to inject the gas housed in the housing space into the interior of the inflatable portion, the injection part including a hole portion penetrating the injection part and communicating the housing space with outside environment;
   a support structure connected to the band, the support structure comprising a first support plate and a second support plate positioned adjacent one another along the longitudinal direction of the band, the second support plate being movably connected to the first support plate; and
   the inflatable portion being on the first support plate and the injection part being on the second support plate.

2. The hemostatic device according to claim 1, wherein the injection part includes:
   a bottom part on the second support plate, and
   a vertical wall part projecting from the bottom part toward the hole portion, the hole portion being at a top part opposite the bottom part of the injection part.

3. The hemostatic device according to claim 2, wherein an outer periphery of the vertical wall part becomes smaller from the bottom part toward the hole portion such that the vertical wall part is formed in a tapered shape from the bottom part toward the top part.

4. The hemostatic device according to claim 2, wherein the top part possesses a center and the hole portion is the center of the top part.

5. The hemostatic device according to claim 1, wherein the first support plate and the second support plate are more rigid than the band.

6. The hemostatic device according to claim 1, wherein the second support plate comprises:
   an outer surface on which the injection part is disposed, the outer surface facing away from the limb when the band is wrapped around the site of the limb,
   an inner surface opposing the outer surface and facing towards the limb, and
   a cushioning member configured to alleviate a contact force transmitted from the second surface to the limb on the inner surface.

7. The hemostatic device according to claim 1, wherein the second support plate comprises an inner surface, the second support plate protruding outward to create a recess between the limb and the inner surface of the second support plate when the band is wrapped around and secured to the limb.

8. The hemostatic device according to claim 1, further comprising
   a tube that is connected to the inflatable portion and the injection part to allow the inflatable portion to communicate with the interior of the injection part,
   the first support plate possessing an inner surface that faces the limb when the band is wrapped around and secured to the limb, the first support plate comprising a first protrusion and a second protrusion on the inner surface of the first support plate, the first protrusion being closer to the second support plate than the second protrusion, the first and second protrusions being spaced apart from one another to interpose the inflatable portion between the first protrusion and the second protrusion in the longitudinal direction of the band.

9. The hemostatic device according to claim 8, wherein the tube penetrate through the first protrusion.

10. The hemostatic device according to claim 8, wherein the first support plate comprises an auxiliary pressing portion configured to direct a pressing direction of the inflatable portion in an inflated state toward the site where bleeding is to be stopped.

11. The hemostatic device according to claim 1, wherein the second support plate comprises a connecting member movably connected to the band.

12. A hemostatic device comprising:
a band configured to be wrapped around a limb of a living body at a site of the living body where bleeding is to be stopped, the band possessing a first end and a second end, the band extending in a longitudinal direction from the first end to the second end;
a first support plate connected to the first end of the band, the first support plate possessing an inner surface facing toward the limb when the band is wrapped around the limb and an outer surface facing away from the limb when the band is wrapped around the limb;
a second support plate connected to the second end of the band and connected to first support plate, the second support plate possessing an inner surface facing toward the limb when the band is wrapped around the limb and an outer surface facing away from the limb when the band is wrapped around the limb;
the first and second support plates being more rigid than the band;
an inflator on the inner surface of the first support plate so that when the band is wrapped around the limb of the living body the inflator is positioned between the first support plate and the limb of the living body, the inflator comprising an interior and an exterior, the inflator being inflated by injection of gas into the interior to expand the exterior and cause the inflator to press the site where bleeding is to be stopped;
an injector on the outer surface of the second support plate so that when the band is wrapped around the limb of the living body the second support plate is positioned between the injector and the limb of the living body, the injector comprising a bottom part, a vertical wall and a top part collectively defining an interior space configured to house a gas, the injection part comprising a hole, the outside environment communicating with the interior space of the injection part via the hole;
a tube connecting the interior of the inflator to the interior space of the injector; and
the injector being configured to inject the gas housed in the housing space into the interior of the inflatable portion through the tube when the hole is covered and the vertical wall of the injector is simultaneously pressed.

13. The hemostatic device according to claim 12, wherein the second support plate is connected to the band via a connecting member.

14. The hemostatic device according to claim 12, wherein the hole is through a center of the top part of the injector.

15. The hemostatic device according to claim 12, wherein the hole is a first hole on the vertical wall of the injector, and
the injector comprises a second hole spaced apart from the first hole on the vertical wall of the injector, the injector being configured to inject the gas housed in the housing space into the interior of the inflatable portion through the tube when the first and second holes are covered and a pinching operation is applied to the vertical wall of the injector.

16. The hemostatic device according to claim 12, wherein the tube comprises a back flow preventer configured to prevent gas from flowing from the interior of the inflator to the interior space of the injector.

17. The hemostatic device according to claim 12, wherein the inflator is a gas permeable material that allows the gas in the interior of the inflator to pass through the inflator to the outside environment.

18. The hemostatic device according to claim 12, wherein the first support plate comprises a first protrusion and a second protrusion on the inner surface of the first support plate, the first protrusion being closer to the second support plate than the second protrusion, the first and second protrusions being spaced apart from one another to interpose the inflator between the first protrusion and the second protrusion in the longitudinal direction of the band, the first and second protrusions extending by a distance such that the inflator does not apply pressure to the limb when the inflator is deflated and the inflator applies pressure to the limb when the inflator is inflated.

19. A method comprising:
wrapping a band of a hemostatic device around a limb of a living body at a site on the living body at which bleeding is to be stopped, the hemostatic device comprising: an inflatable portion; a support structure connected to the band; and an injection portion, the support structure comprising a first support plate and a second support plate positioned adjacent one another along a longitudinal direction of the band, the second support plate being movably connected to the first support plate, the inflatable portion comprising an outer wall defining an interior space, the inflatable portion being deflated when the band is wrapped around the limb of the living body, the injection portion comprising an outwardly protruding vertical wall and a hole, the inflatable portion being on the first support plate and the injection portion being on the second support plate;
pressing the outwardly protruding vertical wall of the injection portion while simultaneously covering the hole to deform the injection portion towards the limb of the living body;
the pressing of the outwardly protruding vertical wall of the injection portion causing gas to enter the interior space of the inflatable portion, inflate the inflatable portion and apply pressure to the site on the limb of the living body to stop bleeding at the bleeding site of the limb; and
gradually reducing the pressure applied to the limb.

20. The method according to claim 19, wherein the inflatable portion includes an inwardly facing surface that faces the limb of the living body when the band is wrapped around the limb and an outwardly facing surface that faces the first support plate positioned in overlying relation to the inflatable portion, the inflatable portion pressing outwardly against the first support plate during the inflation of the inflatable portion, and the injection portion overlaying the second support plate when the band is wrapped around the limb, the second support plate being separate and spaced from the first support plate.

\* \* \* \* \*